United States Patent [19]
Ikeda et al.

[11] Patent Number: 5,276,189
[45] Date of Patent: Jan. 4, 1994

[54] PROCESS FOR THE TREATMENT OF QUATERNARY ONIUM SALTS AND ITS APPLICATION TO THE PREPARATION OF HEXAFLUOROPROPYLENE OXIDE

[75] Inventors: Masanori Ikeda; Yoshio Suzuki, both of Shizuoka; Atsushi Aoshima, Kanagawa, all of Japan

[73] Assignee: Asahi Kasei Kogyo K.K., Osaka, Japan

[21] Appl. No.: 882,761

[22] Filed: May 11, 1992

Related U.S. Application Data

[63] Continuation of Ser. No. 426,259, Oct. 25, 1989, abandoned.

[30] Foreign Application Priority Data

Oct. 25, 1988 [JP] Japan .................. 63-267152

[51] Int. Cl.$^5$ .................. C07C 211/63; C07F 9/54
[52] U.S. Cl. .................. 564/281; 564/291; 564/296; 568/9; 568/11
[58] Field of Search .................. 564/281, 291, 296; 568/9, 11

[56] References Cited

U.S. PATENT DOCUMENTS

| | | | |
|---|---|---|---|
| 2,256,958 | 9/1941 | Muskat | 564/296 |
| 2,727,923 | 12/1955 | Husted | 564/291 |
| 2,961,466 | 11/1960 | Nielsen | 260/567.6 |
| 3,227,748 | 1/1966 | Bragdon et al. | 260/501 |
| 3,660,354 | 5/1972 | Uelzmann | 564/291 |
| 4,623,487 | 11/1986 | Cope | 562/605 |

FOREIGN PATENT DOCUMENTS

| | | |
|---|---|---|
| 520664 | 1/1956 | Canada .................. 564/296 |
| 0100488 | 2/1984 | European Pat. Off. . |
| 0194681 | 9/1986 | European Pat. Off. . |
| 0064293 | 10/1986 | European Pat. Off. . |
| 0269949 | 6/1988 | European Pat. Off. . |
| 0153807 | 3/1982 | German Democratic Rep. . |

OTHER PUBLICATIONS

"Phase Transfer Catalysis, Principles and Techniques", Starks et al, p. 8, Academic Press (1978).
Kinetics of the Reaction of Cyclohexyl Bromide with Tetra-n-propylammonium Thophenoxide in Methanol, Dimethylformamide, and Molten Triethyl-n-hexylammonium Triethyl-n-hexylboride, W. T. Ford, et al, Journal of American Chemical Society, 95, 7381 (1973).
CA 106:33957c, Recovery of Fluoro surfactants, Cope, C. S., p. 37, 1987.

Primary Examiner—C. Warren Ivy
Assistant Examiner—Ba K. Trinh
Attorney, Agent, or Firm—Sughrue, Mion, Zinn, Macpeak & Seas

[57] ABSTRACT

A process for the treatment of a quaternary onium salt is described. The process comprises the steps of (i) contacting an organic phase soaringly miscible in water containing a quaternary onium fluorine-containing carboxylate of $RfCO_2^- + AR^1R^2R^3R^4$ as defined in the present Specification with an aqueous phase containing a thiocyanate ion to form a quaternary onium thiocyanate in the organic phase and (ii) contacting the organic phase containing the quaternary onium thiocyanate with an aqueous solution containing a water-soluble oxidizing agent to decompose the thiocyanate ion and to form an easily ion exchangeable quaternary onium salt. Also, applications of this treatment to a process for preparing hexafluoropropylene oxide from hexafluoropropylene in a two-phase system of an aqueous phase and an organic phase by using a hypochlorite as an oxidizing agent in the presence of a quaternary onium salt as a catalyst are described.

20 Claims, 5 Drawing Sheets

PROCESS FOR THE TREATMENT OF QUATERNARY ONIUM SALTS AND ITS APPLICATION TO THE PREPARATION OF HEXAFLUOROPROPYLENE OXIDE

This is a continuation of application Ser. No. 07/426,259 filed Oct. 25, 1989 now abandoned.

FIELD OF THE INVENTION

The present invention relates to a process for the treatment of a quaternary onium salt. More specifically, it relates to a process for separating the polyfluorocarboxylate anion of $RfCO_2^-$ from a quaternary onium fluorine-containing carboxylate represented by formula [I]

$$RfCO_2^- {}^+AR^1R^2R^3R^4 \qquad [I]$$

wherein

A is a nitrogen atom or a phosphorus atom;
$R^1$, $R^2$, $R^3$ and $R^4$ may be the same or difficult and each is a hydrocarbon group which is unsubstituted or substituted by a functional group inert to the reaction conditions and may contain another onium ion, the total number of carbon atoms contained in $R^1$, $R^2$ and $R^3$ and $R^4$ being at least 8 per onium ion, and $R^1$ and $R^2$ or $R^1$, $R^2$ and $R^3$ or $R^1$, $R^2$, $R^3$ and $R^4$ may combine to form a heterocyclic ring; and $RfCO_2^-$ is a polyfluorocarboxylale anion having from 2 to 15 carbon atoms, to give an easily ion exchangeable quaternary onium salt and its application to the preparation of hexafluoropropylene oxide from hexafluoropropylene.

BACKGROUND OF THE INVENTION

Application of quaternary onium salts

Quaternary onium salts are useful substances as phase transfer catalysts and extracting agents for various anions in an aqueous phase using their ion exchange-ability.

When the quaternary onium salts are tried to be used in the fluorine chemistry, the quaternary onium cation of $^+AR^1R^2R^3R^4$ (hereinafter referred to as "$Q^+$") in formula [I] and the polyfluorocarboxylate anion of $RfCO_2^-$ (hereinafter simply referred to as "$RfCO_2^-$") form a very stable ion pair in a hydrophobic organic solvent and it was found to be difficult to ion exchange this $RfCO_2^-$ with another anion. Thus, it is necessary to exchange the $RfCO_2^-$ with an easily ion exchangeable anion by some method since in the extraction or the phase transfer catalytic reaction $RfCO_2^-Q^+$ as such cannot repeatedly be used. For example, in the fields as will be described below, the development of techniques for converting the quaternary onium fluorine-containing carboxylate of formula [I] to an easily ion exchangeable quaternary onium salt is demanded.

(1) Recovery of polyfluorocarboxylic acids

Polyfluorocarboxylic acids are useful compounds as fluorine-containing surfactants and solvents and are very expensive, and an effective method of recovering them is desired but at present no excellent method is found. As described above, since the polyfluorocarboxylate anion is confirmed to form a very stable ion pair with $Q^+$ in an organic phase, it is possible to simply extract the polyfluorocarboxylate anion as the counter ion to $Q^+$ in the organic phase by contacting an aqueous solution or an emulsion containing a polyfluorocarboxylate salt with an organic phase containing $Q^+$.

However, an effective method for removing the polyfluorocarboxylate anion from a stable ion pair of $Q^+$ and a polyfluorocarboxylate anion to form an easily ion exchangeable quaternary onium salt is not known at present, and accordingly, a complicated, costly method is disadvantageously forced to be employed for the recovery of the polyfluorocarboxylate anion by using a quaternary onium salt.

As a known method of recovering a polyfluorocarboxylic acid from an aqueous medium by using a quaternary onium salt, there can be mentioned, for example, a method of recovering a fluoroalkanoic acid from the aqueous medium used in the polymerization of a fluoroolefin by using a salt of the fluoroalkanoic acid as a surfactant as described in Japanese Patent Publication (OPI) No. 246142/1986. According to this method a quaternary ammonium salt of the fluoroalkanoic acid is firstly formed and secondly an aqueous 50% by weight sulfuric acid solution is added to the quaternary ammonium salt and thirdly the mixture solution is heated to distill the fluoroalkanoic acid. This method is complicated and moreover, requires the treatment of the quaternary onium salt in an aqueous highly concentrated sulfuric acid solution at a high temperature of at least 100° C. for a long period of time and the decomposition of the part of the quaternary onium cation cannot be avoided. Thus, this method cannot be said to be economically advantageous.

On the other hand, when an effective method of treating a stable ion pair of $Q^+$ and a polyfluorocarboxylate anion is established, a process for economically recovering a polyfluorocarboxylic acid by using a quaternary onium salt will be possible.

(2) Activation of the catalyst in a phase transfer catalytic reaction

In the phase transfer catalytic reaction using a quaternary onium salt as the catalyst, when $RfCO_2^-$ is formed as the main product or as the by-product, a stable ion pair of $RfCO_2^-Q^+$ is formed and the ion exchange-ability of the catalyst is decreased to suppress the activity of the phase transfer catalytic reaction. In such a case in order to economically conduct the phase transfer catalytic reaction by effectively using $Q^+$, it is desired to develop an economical method to activate the quaternary onium salt with decreased catalytic activity to form an easily ion exchangeable and highly active quaternary onium salt.

As the method of converting a quaternary onium salt forming a stable ion pair to an easily ion exchangeable quaternary onium salt, there are known, for example, a method using dimethylsulfuric acid by Bränström (A. Bränström, "Preparative Ion Pair Extraction", pp 139-148, Apotekarsocieteten/Hassle, Lakemedel, Sweden, 1974) and a method using silver oxide [W. T. Ford, Journal of American Chemical Society, 95, 7381 (1973)]. However, these methods which use toxic reagents and expensive reagents and whose procedures are complicated cannot be said to be economically advantageous because of the high cost of the treatment.

SUMMARY OF THE INVENTION

Extensive investigations to develop a method of efficiently removing $RfCO_2^-$ from a quaternary fluorine-containing carboxylate of formula [I] under mild conditions to form an easily ion exchangeable quaternary onium salt were conducted. Firstly, a method of separating $RfCO_2^-$ from $RfCO_2^-Q^+$ forming a stable ion pair was examined. However, the ion exchange of $RfCO_2^-$ with $OH^-$ or $Cl^-$ was conducted in vain because $RfCO_2^-Q^+$ forms a very stable ion pair. Then, when an organic phase containing $RfCO_2^-Q^+$ was contacted with an aqueous phase containing a thiocyanate ion ($SCN^-$) surprisingly it was found that the $RfCO_2^-$ in $RfCO_2^-Q^+$ can be simply ion exchanged with $SCN^-$. As a result, a quaternary onium thiocyanate is formed in the organic phase and $RfCO_2^-$ migrates into the aqueous phase and thus, $RfCO_2^-$ can be easily recovered from the aqueous phase.

Further, the quaternary onium thiocyanate formed in the organic phase forms a very stable ion pair and it was difficult to exchange the quaternary onium thiocyanate as such with various anions in the aqueous phase. However, when the organic phase containing a quaternary onium thiocyanate was contacted with an aqueous phase containing a water-soluble oxidizing agent, it was found that $SCN^-$ can easily be decomposed under mild conditions to form an active quaternary onium salt in the organic phase which is easily ion exchangeable with various anions.

According to the present invention there are provided a process for the treatment of a quaternary onium salt which comprises the steps of:

(i) contacting an organic phase sparingly miscible in water containing a quaternary onium fluorine-containing carboxylate represented by formula [I]

wherein
A is a nitrogen atom or a phosphorus atom;
$R^1$, $R^2$, $R^3$ and $R^4$ may be the same or difficult and each is a hydrocarbon group which is unsubstituted or substituted by a functional group inert to the reaction conditions and may contain another onium ion, the total number of carbon atoms contained in $R^1$, $R^2$, $R^3$ and $R^4$ being at least 8 per onium ion, and $R^1$ and $R^2$ or $R^1$, $R^2$ and $R^3$ or $R^1$, $R^2$, $R^3$ and $R^4$ may combine to form a heterocyclic ring; and
$RfCO_2^-$ is a polyfluorocarboxylate anion having from 2 to 15 carbon atoms, with an aqueous phase containing a thiocyanate ion to form a quaternary onium thiocyanate in the organic phase; and (ii) contacting the organic phase containing the quaternary onium thiocyanate with an aqueous solution containing a water-soluble oxidizing agent to decompose a thiocyanate ion and to form an easily ion exchangeable quaternary onium salt; and a process for preparing hexafluoropropylene oxide from hexafluoropropylene in a two-phase system of an organic phase sparingly miscible in water containing a quaternary onium salt catalyst having a quaternary onium cation of $+AR^1R^2R^3R^4$ in formula [I] and an aqueous phase containing a hypochlorite salt as an oxidizing agent, which comprises the above described treatment of the quaternary onium salt.

DETAILED DESCRIPTION OF THE INVENTION

Figure 1:
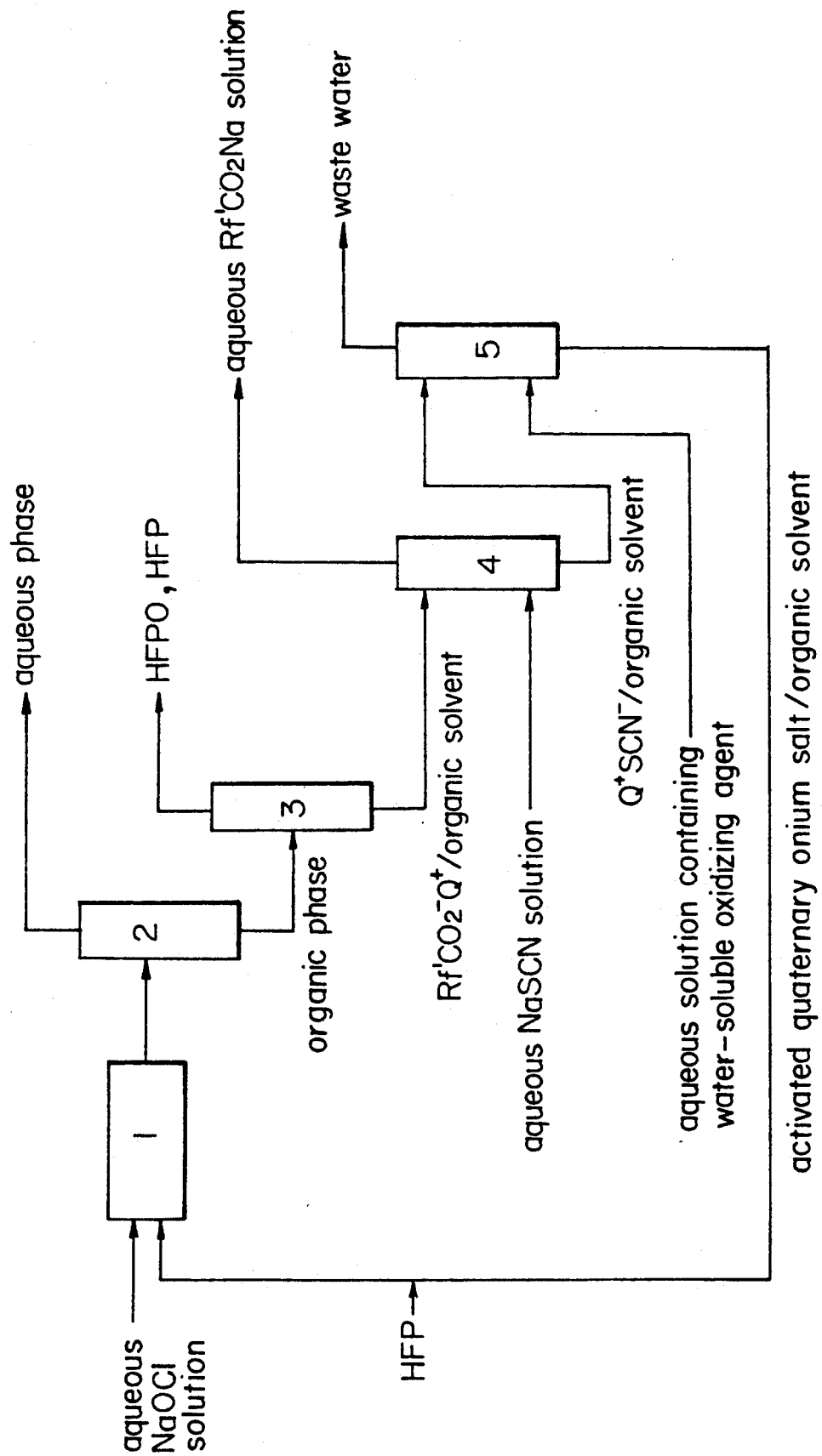
FIG. 1 is one example of block flow diagram illustrating a process for the preparation of hexafluoropropylene oxide from hexafluoropropylene comprising a step for activating the quaternary onium salt catalyst with decreased catalytic activity.

In carrying out the treatment of a quaternary onium salt according to the present invention, it is enough that the two-phase reaction of an organic phase sparingly miscible in water and an aqueous phase is twice conducted, and the organic phase containing the activated onium salt formed by the treatment of the present invention as such can repeatedly be used in a phase transfer catalytic reaction or an ion extraction. Further, according to the present invention $RfCO_2^-$ can easily be collected from the aqueous phase obtained by step (i). Thus, it is possible to simply and economically conduct a separation process and a phase transfer catalytic reaction.

In the process of the present invention a hydrophobic quaternary onium cation of $+AR^1R^2R^3R^4$ in formula [I], wherein
A is a nitrogen atom or a phosphorus atom;
$R^1$, $R^2$, $R^3$ and $R^4$ may be the same or different and each is a hydrocarbon group which is unsubstituted or substituted by a functional group inert under the reaction conditions,
is employed.

The type and length of the hydrocarbon group are appropriately selected depending on the type of solvent used, the object of use and so forth. Examples of such hydrocarbon groups include an alkyl group, an alkenyl group, a cycloalkyl group, a cycloalkenyl group, an aryl group, an aralkyl group and alkenylaryl group, of these groups, an alkyl group, an aryl group and an aralkyl group are particularly preferred. With regard to the length of the hydrocarbon group, the total number of carbon atoms contained in $R^1$, $R^2$, $R^3$ and $R^4$ is at least 8, usually from 8 to 70, preferably from 10 to 50 and particularly preferably 12 to 40, per onium ion. The inert functional group which can be used as substituents for the hydrocarbon group is limited depending on the reaction conditions. Usually a halogen atom, an acyl group, an ether group, an ester group, a nitrile group and an alkoxy group are used. $R^1$ and $R^2$ or $R^1$, $R^2$ and $R^3$ or $R^1$, $R^2$, $R^3$ and $R^4$ may combine together to form a heterocyclic ring and also, $R^1$, $R^2$, $R^3$ or $R^4$ may contain another onium ion.

Exemplary hydrophobic quaternary onium cations which can be used in the present invention include quaternary ammonium ions such as a tetra-n-propylammonium ion, a tetra-n-butylammonium ion, a tri-n-octylmethylammonium ion, a tetra-n-octylammonium ion, a tetra-n-decylammonium ion, a cetyltrimethylammonium ion, a tri-n-decylmethylammonium ion, a benzyltrimethylammonium ion, a benzyltriethylammonium ion, a cetylbenzyldimethylammonium ion, a cetylpyridinium ion, a n-dodecylpyridinium ion, phenyltrimethylammonium ion, a phenyltriethylammonium ion, an N-benzylpicolinium ion, a pentamethonium ion and a hexamethonium ion; and quaternary phosphonium ions such as a tetra-n-butylphosphonium ion, a tri-n-octylmethylphosphonium ion, tri-n-octylethylphosphonium ion, a cetyltriethylphosphonium ion, a cetyltri-n-butylphosphonium ion, a n-butyltriphenylphosphonium ion, a n-amyltriphenylphosphonium ion, a n-hexyltriphenylphosphonium ion, a n-heptyltriphenylphosphonium ion, a methyltriphenylphosphonium ion, a benzyltriphenylphosphonium ion and a tetraphenylphosphonium ion.

As $RfCO_2^-$ in the quaternary onium fluorine-containing carboxylate of formula III, a polyfluorocarboxylate anion having 2 to 15 carbon atoms is used. The polyfluorocarboxylate anion is a carboxylate anion having 2 to 15 carbon atoms in which a plurality of hydrogen atoms have been substituted by fluorine atoms, preferably one in which the number of fluorine atoms is at least that of hydrogen atoms and may have a halogen atom other than fluorine atom and a substituent such an ether group which are inert under the conditions of the present invention. Of these polyfluorocarboxylate anions, particularly preferred is one in which at least one fluorine atom is bonded to the carbon atom bonded to the carbonyl group.

The number of carbon atoms in the polyfluorocarboxylate anion which can be used in the present invention is typically from 2 to 15, preferably from 2 to 12.

Exemplary polyfluorocarboxylate anions include a tri-fluoroacetate anion, a 2,3,3,3-tetrafluoropropionate anion, a 2-chloro-2,3,3,3-tetrafluoropropionate anion, a 2,2,3,3-tetrafluoropropionate anion, a pentafluoropropionate anion, a perfluorovalerate anion, a long chain polyfluorocarboxylate anion represented by the following formula [III]

$$Z-Y-CO_2H \quad \text{[II]}$$

wherein
Y is a perfluorinated linear or branched alkylene group having 5 to 10 carbon atoms; and
Z is a hydrogen atom, a fluorine atom or a chlorine atom, which is useful as a fluorine-type anionic surfactant whose representative example is a perfluorooctanate anion; a perfluoroethercarboxylate anion whose representative example is a perfluoro-2-methyl-3-oxahexanate anion; an aromatic carboxylate anion substituted with a perfluoroalkyl group or a perfluoroalkylene group and a nucleus-fluorinated aromatic carboxylate anion whose representative example is a pentafluorobenzoate anion.

The quaternary onium salt which can be employed in the present invention may contain an anion other than $RfCO_2^-$ since most of such an anion together with $RfCO_2^-$ can be ion exchanged with $SCN^-$ without causing any problem. However, when the anion other than $RfCO_2^-$ contained in the quaternary onium salt is an oxidative anion such as a hypochlorite ion and a nitrate ion, part of $SCN^-$ is decomposed by the oxidative anion in the ion exchange reaction between $RfCO_2^-Q^+$ and $SCN^-$. Thus, when a large amount of the oxidative anion is present in the quaternary onium salt, it is effective to treat the organic phase containing the quaternary onium salt with an aqueous solution containing a reducing agent such as sodium sulfite and sodium thiosulfate before contacting the organic phase with an aqueous solution containing $SCN^-$ or to add the reducing agent to the aqueous solution containing $SCN^-$ to suppress the decomposition of $SCN^-$.

The organic phase sparingly miscible in water which can be employed in the present invention is a phase containing a quaternary onium salt of formula [I] and forming a phase different from an aqueous phase and usually consists of the quaternary onium salt and an organic solvent sparingly miscible in water. In some cases, the main component of the organic phase may be a liquid quaternary onium salt and the organic phase may consist of a plurality of organic phases sparingly miscible in water.

Exemplary organic solvents sparingly miscible in water which are used to form the organic phase include aliphatic hydrocarbons such as n-hexane, n-octane and n-decane; alicyclic hydrocarbons such as cyclohexane, methylcyclohexane and decalin; aromatic hydrocarbons such as benzene, toluene and xylene; ethers such as diisopropyl ether and di-n-butyl ether; chlorinated hydrocarbons such as methylene chloride, chloroform, carbon tetrachloride, 1,2-dichloroethane and chlorobenzene; hydrocarbons substituted with a chlorine atom and a fluorine atom such as 1,2-dichloro-1,1,2,2-tetrafluoroethane, fluorotrichloromethane, 1,1,2-trichloro-1,2,2-trifluoroethane and 1,1,2,2-tetrachloro-1,2-difluoroethane; perfluorocarbons or polyfluorocarbons which may contain an oxygen atom such as perfluorocyclobutane, perfluorodimethylcyclobutane, perfluorohexane, perfluorooctane, perfluorodecane, 1,3-di(trifluoromethyl)benzene, hexafluorobenzene 2H-tetradecafluoro-5-(trifluoromethyl)-3,6-dioxanone and perfluoro-2-butyltetrahydrofuran; and mixtures thereof. The organic solvent is appropriately selected taking into account the solubility of the quaternary onium salts, the phase separability from the aqueous phase, the operation temperature for conducting the method of the present invention and the conditions under which the activated onium salts obtained by the treatment of the present invention are actually used in a phase transfer catalytic reaction or in an extraction. Of the above described solvents, chlorinated hydrocarbons are suitable for use in the present invention because of the high solubilities of $RfCO_2^-Q^+$ therein, and also, fluorine-containing solvents are suitable for use in the present invention because of their good phase separability from the aqueous phase and the high solubilities of the fluorine-containing reactants and the products therein when used in the phase transfer catalytic reaction.

The sources of thiocyanate ion which can be used in the present invention may be any compounds capable of forming thiocyanate ion in an aqueous solution and include various water-soluble thiocyanate salts.

Exemplary water-soluble thiocyanate salts include alkali metal thiocyanates such as sodium thiocyanate and potassium thiocyanate; alkaline earth metal thiocyanates such as calcium thiocyanate and barium thiocyanate; zinc thiocyanate, iron thiocyanate and ammonium thiocyanate. Of these thiocyanates, sodium thiocyanate, potassium thiocyanate and ammonium thiocyanate, which are commercially used in large quantities, are preferred as the thiocyanic ion source in consideration of their price and easy availability.

The mole ratio of $SCN^-$ to $RfCO_2^-Q^+$ is not critical but when it is less than one, complete exchange of $RfCO_2^-$ cannot be realized. Accordingly, in order to exchange substantially all of the $RfCO_2^-$ with $SCN^-$, the mole ratio of $SCN^-$ to $RfCO_2^-Q^+$ is required to be at least one. In taking account of the cost of $SCN^-$ and ease of ion exchange reaction, practically the mole ratio of $SCN^-$ to $RfCO_2^-Q^+$ is typically in the range of from 0.5 to 20, preferably from 0.8 to 10, particularly preferably from 1 to 4.

When an anion other than $RfCO_2^-$ is present as a counter ion of $Q^+$ in the quarternary onium salt, in order to exchange substantially all of the $RfCO_2^-$ with $SCN^-$, it is necessary that the mole ratio of $SCN^-$ to $Q^+$ is at least one. Practically the mole ratio of $SCN^-$ to $Q^+$ is typically from 0.5 to 20, preferably from 0.8 to 10, particularly from 1 to 4.

The reaction between the organic phase containing $RfCO_2^-Q^+$ and the aqueous phase containing $SCN^-$ can be carried out by a number of methods including a batch method, a semi-flow method and a flow method which are employed in the conventional two-liquid phase reaction. Commercially it is preferred to employ the flow method capable of continuous operation such as a counter-current multistage contacting reaction system and continuously stirring vessel type reaction system and particularly the flow method of counter-current multistage contacting reaction system is advantageous from the viewpoint of using smaller amounts of $SCN^-$ against $RfCO_2^-Q^+$.

As counter-current multistage reaction devices there can be used a mixer-settler, a rotary disk extractor, a perforated plate extractor, a stirring extraction column and so forth which are usually employed in extraction procedure.

The temperature for the reaction between the organic phase containing $RfCO_2^-Q^+$ and the aqueous phase containing $SCN^-$ may be around room temperature and is not particularly limited. When the temperature is too low, the rate of ion exchange becomes slow and in extreme cases, the aqueous phase and the organic phase freeze. On the other hand, when the temperature is too high, the vaporization of the solvent is brought about. Thus, the temperature is usually within the range of from $-10°$ C. to $100°$ C., preferably within the range of from $-5°$ C. to $80°$ C.

Heretofore, it is known as a method for decomposing $SCN^-$ that the $SCN^-$ in an aqueous solution is decomposed by sodium hypochlorite. As a result of investigations to develop a method of decomposing $SCN^-$ in a hydrophobic solvent it has now been found that various water-soluble oxidizing agents including sodium hypochlorite can efficiently decompose quaternary onium thiocyanates in a phase other than an aqueous phase, that is, in an organic phase soaringly miscible in water.

The water-soluble oxidizing agents which can be employed in the present invention include various oxidizing agents capable of decomposing the thiocyanate ion structure by the reaction with the thiocyanate ion.

Exemplary oxidizing agents include alkali metal or alkaline earth metal hypochlorites such as lithium hypochlorite, sodium hypochlorite, potassium hypochlorite, magnesium hypochlorite, calcium hypochlorite and barium hypochlorite; alkali metal or alkaline earth metal chlorate such as sodium chlorate, potassium chlorate and calcium chlorate; oxidizing agents of chlorine type such as hypochloric acid and chlorine water; oxidizing agents of peroxide type such as tert-butyl hydroperoxide and hydrogen peroxide; oxidizing agents of nitric acid type such as nitric acid, nitrous acid and sodium nitrate; and oxidizing agents of persulfuric acid type such as sodium persulfate. Of these compounds, inorganic oxidizing agents are preferred because of their easy availability and their small residual amount in the organic phase, and oxidizing agents of chlorine type and alkali metal or alkaline earth metal hypochlorites such as sodium hypochlorite and calcium hypochlorite are particularly suitable for use in the present invention because they are commercially available and excellent in safety, handling and reactivity.

Further, when the activated quaternary onium salt obtained by the treatment of the present invention is employed for the operation in the presence of a water-soluble oxidizing agent, for example, for extraction and phase transfer catalytic reaction, the step for contacting $Q^+SCN^-$ with an aqueous solution containing a water-soluble oxidizing agent can be deleted. That is, when the organic phase containing $Q^+SCN^-$ is used in the presence of a water-soluble oxidizing agent for a certain object, the formation of an activated quaternary onium salt by the decomposition of $Q^+SCN^-$ and the object can be simultaneously attained.

For example, the aqueous solution containing the water-soluble oxidizing agent which can be employed in the present invention may contain a polyfluorocarboxylate ion ($RfCO_2^-$) in the quaternary onium fluorine-containing carboxylate of formula [I]. In such a case the decomposition of $SCN^-$ in the organic phase and the extraction of $RfCO_2^-$ into the organic phase are simultaneously carried out.

In the present invention the mole ratio of the water-soluble oxidizing agent to be reacted to the quaternary onium thiocyanate is not subject to any limitations. In order to sufficiently carry out the decomposition of $SCN^-$, the water-soluble oxidizing agent is typically employed in an amount of at least one mole per mole of the quaternary onium thiocyanate. Practically from the standpoints of economy and reaction efficiency the water-soluble oxidizing agent is preferably employed in an amount of from 2 to 100 moles, preferably from 2 to 20 moles, per mole of the quaternary onium thiocyanate, with the range of from 3 to 15 moles being particularly preferred.

As the method for the reaction between an organic phase containing the quaternary onium thiocyanate and an aqueous phase containing the water-soluble oxidizing agent, there can be employed the same method for the reaction between an organic phase containing the above described $RfCO_2^-Q^+$ and an aqueous phase containing $SCN^-$.

The temperature for the reaction between the organic phase containing a quaternary onium thiocyanate and the aqueous phase containing a water-soluble oxidizing agent may be around room temperature and is not subject to any limitations. When the temperature is too low, the rate of reaction becomes slow and in extreme cases, the aqueous phase and the organic phase freeze. On the other hand, when the temperature is too high, the vaporization of the solvent is brought about. Thus, the temperature is usually within the range of $-10°$ C. to $100°$ C., preferably within the range of from $-5°$ C. to $60°$ C.

As described above, the treatment of the quaternary onium salt according to the present invention can be advantageously applied to a separation process and a process of phase transfer catalytic reaction which use the characteristic feature of the quaternary onium salt.

Applications of the treatment of the quaternary onium salt to a process for the preparation of hexafluoropropylene oxide from hexafluoropropylene will now be explained in detail.

[A] Activation of the catalyst used in the preparation of hexafluoropropylene oxide Hexafluoropropylene oxide (hereinafter referred to as "HFPO") is an important starting material useful for preparing various high functional fluorine-containing materials such as perfluoro lubricant oil, perfluoro elastomer and perfluoro ion exchange resin.

As for the method of preparing HFPO, for example, in European Patent No. 0,064,293 and Canadian Patent No. 1,220,216 there is disclosed a process for preparing HFPO from hexafluoropropylene (hereinafter referred to as "HFP") under mild conditions in high yields which comprises epoxidizing HFP in a two-phase system of an aqueous phase and an organic phase using a hypochlorite salt dissolved or dispersed in the aqueous phase in the presence of a variety of phase transfer catalysts such as quaternary ammonium salts and quaternary phosphonium salts. As a result of further investigations to establish a commercially advantageous process for preparing HFPO from HFP by the phase transfer catalytic reaction using a hypochlorite salt as the oxidizing agent, it has found that, when the hydrophobic quaternary ammonium salt and the hydrophobic quaternary phosphonium salt containing the quaternary onium cation (hereinafter referred to as "$Q^+$") in formula [I] are repeatedly used as catalysts in the above described reaction, their catalytic activity is slowly decreased and a certain level of the HFP conversion cannot be obtained over a long period of time. Accordingly, in order to maintain a certain level of the HFP conversion in repeating the preparation of HFPO from HFP it is necessary to activate the quaternary onium salt with decreased catalytic activity or to replace the whole or part of the quaternary onium salt with decreased catalytic activity by a new quaternary onium salt or to add a new quaternary onium salt to the quaternary onium salt with decreased catalytic activity. However, the use of a new quaternary onium salt for maintaining a certain level of catalytic activity increases the cost of catalyst and causes difficulty in controlling the reaction conditions and unfavorably requires complicated procedure. Thus, it is necessary to develop a method of activate the quaternary onium salt with decreased catalytic activity for an economical preparation of HFPO from HFP by repeatedly using the quaternary onium salt as a phase transfer catalyst.

Investigations of the cause of decrease in catalytic activity of the quarternary onium salt catalyst have revealed that fluorine-containing carboxylate anions showing a specific absorption band at 1695 cm$^{-1}$ in the infrared absorption spectrum are present as a counter ion to $Q^+$ in the quaternary onium salt with decreased catalytic activity and these fluorine-containing carboxylate anions (hereinafter referred to as "$RfCO_2^-$") are assumed to mainly comprise a plurality of polyfluorocarboxylates having three carbons such as $CF_3CFXCO_2^-$ wherein X is F, Cl or H and $CF_3CO_2^-$ and the amount of $CF_3CFXCO_2^-$ is also assumed to be more than that of $CF_3CO_2^-$ from the $^{19}$F-NMR spectrum of the quaternary onium salt with decreased catalytic activity. The $CF_3CF_2CO_2^-$ may be considered to derive from $CF_3CF_2COF$ formed by the isomerization of HFPO. On the other hand, the $CF_3CO_2^-$ and other $RfCO_2^-$ may be considered to be formed by the decomposition of HFP or HFPO although their formation mechanism in detail is not clear. Further, it has been found that, when an organic phase containing $RfCO_2^-Q^+$ is contacted with an aqueous solution containing a large amount of NaCl or NAOH in order to obtain $Q^+Cl^-$ or $Q^+OH^-$ having high phase transfer catalytic activity from $RfCO_2^-Q^+$ by ion exchange reaction, the ion exchange reaction hardly progresses and $RfCO_2^-Q^+$ is present as a very stable ion pair.

The reason for the low phase transfer catalytic activity of the quaternary onium salts containing $RfCO_2^-Q^+$ is not clearly confirmed. However, from the above described results, it may be considered that the ion exchange between $RfCO_2^-$ and a hypochlorite ion ($OCl^-$) is difficult to progress due to the formation of a stable ion pair of $RfCO_2^-Q^+$ and as a result, $RfCP_2^-$ cannot sufficiently express the function of a phase transfer catalyst as a medium for transferring $Q^+OCl^-$ from an aqueous phase to an organic phase since $Q^+OCl^-$ is difficult to form. Accordingly, in the preparation of HFPO, in order to activate the quaternary onium salt mainly composed of $RfCO_2^-Q^+$ should be converted to an easily exchangeable quaternary onium salt by some method. However, it is not known to economically advantageously convert a quaternary onium salt forming a highly stable ion pair to an easily ion exchangeable quaternary onium salt such as $Q^+Cl^-$, $Q^+OH^-$ and $Q^+HSO_4^-$.

It has now been found that, when the treatment of the quaternary onium salt of the fluorine-containing carboxylic acid of formula [I] is applied to $RfCO_2^-Q^+$ formed in the preparation of HFPO, the catalytic activity of $RfCO_2^-Q^+$ can be recovered by a very simple procedure to obtain the same catalytic activity as $Q^+Cl^-$ and thus, a process for the preparation of HFPO comprising a step of activating the catalyst has been established.

More specifically, there is provided a process for preparing HFPO from HFP in a two-phase system of an organic phase sparingly miscible in water containing a quaternary onium salt having a cation of $^+AR^1R^2R^3R^4$ in formula [I] and an aqueous phase containing a hypochlorite salt as an oxidizing agent, which comprises the steps of:

(a) contacting the organic phase containing a quaternary onium salt having decreased catalytic activity after the preparation of HFPO with an aqueous phase containing a thiocyanate ion to form a quaternary onium thiocyanate in the organic phase;

(b) contacting the organic phase containing the quaternary onium thiocyanate with an aqueous solution containing a water-soluble oxidizing agent to decompose the thiocyanate ion; and (c) reusing the organic phase thus obtained as the organic phase in the step for preparing HFPO.

In the above described process, steps (a) and (b) can be conducted under the same conditions by the same procedure as in the treatment of the quaternary onium salt of formula [I].

The organic phase, the aqueous phase and the quaternary ammonium salt or the quaternary phosphonium salt which can be employed in the preparation of HFPO are those described in European Patent No. 0,064,293. For example, the organic solvent used for the organic phase is an inert solvent substantially immiscible or sparingly miscible in the aqueous phase and the solvent used is the same type of the solvent which can be used in the above described treatment of the quaternary onium salt. Accordingly, in this process for the preparation of HFPO, the organic solvent used in the step of the preparation of HFPO may be the same or different solvent used in the step of the treatment of the quaternary onium salt but for the simplicity of procedure it is preferred to use the same solvent as far as there is no procedural restriction.

The organic phase in the preparation of HFPO or in the treatment of the quaternary onium salt may be any organic phase containing a quaternary onium salt capable of forming a phase different from an aqueous phase and usually consists of a quaternary onium salt and an organic solvent sparingly miscible in water. The organic phase nay also be a phase whose main component is a liquid quaternary onium salt sparingly miscible in water or a phase consisting of two or more organic chases sparingly miscible in water containing a quaternary onium salt.

The quaternary onium cation in the hydrophobic quaternary ammonium salt or quaternary phosphonium salt which can be employed is a cation of $^+AR^1R^2R^3R^4$ in formula [I]. Various anions can be used as an anion in the quaternary onium salt in the first preparation of HFPO, and typically a halogen ion such as a chlorine ion and a bromine ion, a hydroxyl ion or a hydrogensulfate ion ($HSO_4^-$) is used.

The hypochlorite salt which can be used in the preparation of HFPO is described in European Patent No. 0,064,293. Of them, sodium hypochlorite and calcium hypochlorite are preferred because of their easy availability at a low cost.

in the aqueous phase in the preparation of HFPO in addition to the hypochlorite salt, the presence of an inorganic base such as sodium hydroxide is preferred because the inorganic base advantageously gives a high HFPO selectivity even at a high HFP conversion when the amount of the hypochlorite salt added is small.

The process for preparing HFPO can be carried out by a number of methods including a batch method, a semi-flow method and a flow method.

Part of the quaternary onium salt after the preparation of HFPO is changed to $Rf'CO\ Q^+$ as described above, and when such a quaternary onium salt catalyst is repeatedly used in the preparation of HFPO, the catalytic activity is slowly decreased. The reason for this decrease in catalytic activity is not elucidated but may be considered due to the increase in the ratio of $Rf'CO_2^-Q^+$ in the quaternary onium slat catalyst and that of $Rf'CO_2^-Q^+$ having less ion exchangeability among $Rf'CO_2^-Q^+$.

When the same treatment of the quaternary onium salt of formula [I] is applied to the quaternary onium salt catalyst containing such $Rf'CO_2^-Q^+$, the catalytic activity of the quaternary onium salt catalyst in the preparation of HFPO is recovered and the quaternary onium salt catalyst thus activated can be reused as a catalyst in the preparation of HFPO.

In the treatment of the above described quaternary onium salt, the contact between the organic phase containing $Rf'CO_2^-Q^+$ and an aqueous phase containing a thiocyanate ion may be conducted either before or after the removal of HFPO and unreacted HFP from the organic phase after the preparation of HFPO by, for example, distillation. In some cases a remarkable amount of hypochlorite ions is present in the organic phase containing $Rf'CO_2^-Q^+$ and, if necessary or required, the organic phase may be treated with an aqueous solution of a reducing agent such as sodium sulfite and sodium thiosulfate before contacting with an aqueous solution containing a thiocyanate ion.

The activation of the quaternary onium salt catalyst containing $Rf'CO_2^-Q^+$ can be conducted after every preparation of HFPO or after repeating the preparation of HFPO several times. Or in repeating the preparation of HFPO, part of the quaternary onium salt catalyst containing $Rf'CO_2^-Q^+$ can be withdrawn after every preparation of HFPO, activated and returned to the preparation of HFPO.

With reference to FIG. 1, one embodiment of the above described process will be explained.

Numeral 1 is a step for the preparation of HFPO in a two-phase system and numeral 2 is a step for the phase separation of an organic phase and an aqueous phase as obtained in the preparation of HFPO in step 1 and numeral 3 is a step for the distillation of HFPO and unreacted HFP from the organic phase as obtained in step 2 and numeral 4 is a step for the ion exchange reaction by contacting the bottom solution of the distillation containing $Rf'CO_2^-Q^+$ from step 3 with an aqueous phase containing a thiocyanate ion such as an aqueous sodium thiocyanate solution to form $Q^+SCN^-$ and an aqueous phase containing $Rf'CO_2^-$ such as an aqueous $Rf'CO_2Na$ solution is collected from step 4. Numeral 5 is a step for the decomposition of $SCN^-$ by contacting the organic phase containing $Q^+SCN^-$ from step 4 with an aqueous solution of a water-soluble oxidizing agent such as an aqueous sodium hypochlorite solution to form activated quaternary onium salt in the organic phase which is then reused in step 1, while the aqueous phase thus obtained is discharged as a waste water. The above described steps 1 and 2 can be conducted in separate devices or in one device when step 1 is carried out batchwise.

Usually the preparation of HFPO is carried out in the presence of a hypochlorite salt whose amount is more than that required for the epoxidization of HFP. When the amount of the hypochlorite salt is sufficient for carrying out both the decomposition of $Q^+SCN^-$ and the epoxidization of HFP, it is possible to conduct these two reactions at the same time.

More specifically, in the above described process for the preparation of HFPO, steps (b) and (c) can be carried out at the same time by using the organic phase containing $Q^+SCN^-$ formed in step (a) as the organic phase in the step of preparing HFPO. In this process the mole ratio represented by formula [III] below is typically at least one, preferably from 2 to 100, particularly preferably from 2 to 20.

$$\frac{\left[\begin{array}{c}\text{mole of hypochlorite}\\ \text{ion in aqueous phase}\\ \text{before carrying out}\\ \text{this treatment}\end{array}\right] - \left[\begin{array}{c}\text{mole of } HFP\\ \text{conversion}\end{array}\right]}{\left[\begin{array}{c}\text{mole of } Q^+SCN^-\\ \text{in organic phase}\end{array}\right]} \quad [III]$$

When the above described process is employed, the quaternary onium salt catalyst with decreased catalytic activity can be activated under mild conditions by simple procedure, and an economical process for the preparation of HFPO comprising repeatedly using the quaternary onium salt catalyst is made possible. Further, it is possible to recover $R'CO_2^-$ as a by-product from the aqueous phase after the ion exchange reaction between $Rf'CO_2^-Q^+$ and $SCN^-$.

[B] Removal of polyfluorocarboxylate ions from the aqueous phase used in the preparation of HFPO It is confirmed by the analysis of the aqueous phase after the preparation of HFPO as explained in [A] that the same type of fluorine-containing carboxylate ions as $Rf'CO_2^-$ in $Rf'CO_2^-Q^+$ in the organic phase is present in the aqueous phase. This $Rf'CO_2^-$ which forms an ion pair with a metal cation such as sodium cation is considered to be by-produced in the preparation of HFPO by the same mechanism of formation of $Rf'CO_2^-$ in $Rf'CO_2^-Q^+$ in the organic phase. The composition of $Rf'CO_2^-$ may very depending on the reaction conditions but the ratio of $CF_3CO_2^-$ in $Rf'CO_2^-$ in the aqueous phase is higher compared with that of $Rf'CO_2^-$ in $Rf'CO_2^-Q^+$ in the organic phase. For example, the ratio of $CF_3CO_2^-$ in $Rf'CO_2^-$ in the aqueous phase is 87% as will be shown in Example 17.

It is unfavorable to discharge the aqueous phase containing $Rf'CO_2^-$ from the reaction equipment for the preparation of HFPO from the viewpoint of preservation of the environment and it is necessary to remove $Rf'CO_2^-$ from the aqueous phase by some method. On the other hand, fluorine-containing carboxylic acids such as $Rf'COOH$ are useful as solvents, catalysts and starting materials for producing fluorine-containing compounds. Thus, the isolation of $Rf'COOH$ is economically advantageous.

Heretofore, there are known various methods of isolating a carboxylic acid from an aqueous strongly acidic solution. However, since the aqueous phase after the preparation of HFPO is usually strongly alkaline and its pH is, for example 10 or more, it is necessary to add a large amount of an inorganic acid to the aqueous phase to form an aqueous strongly acidic solution when the above described conventional methods are employed.

As a result of investigations of the method for extracting the $Rf'CO_2^-$ from an aqueous strongly alkaline solution containing $Rf'CO_2^-$ under the alkaline condition it has been found that the above described treatment of the quaternary onium salt of $Rf'CO_2^-Q^+$ with $SCN^-$ and a water-soluble oxidizing agent can be economically applied to the extraction of $Rf'CO_2^-$.

More specifically, there is provided a process for preparing HFPO from HFP in the presence of a catalyst in a two-phase system of an organic phase sparingly miscible in water and an aqueous phase containing a hypochlorite salt as an oxidizing agent which comprises the steps of:

(d) contacting a waste water phase containing a fluorine-containing carboxylate formed as a by-product in the process for preparing HFPO from HFP with an organic phase sparingly miscible in water containing a quaternary onium salt having a cation of $^+AR^1R^2R^3R^4$ in formula [II] to form a quaternary onium fluorine-containing carboxylate in the organic phase;

(e) contacting the organic phase containing the quaternary onium fluorine-containing carboxylate with an aqueous phase containing a thiocyanate ion to form a quaternary onium thiocyanate in the organic phase;

(f) contacting the organic phase containing the quaternary onium thiocyanate with the aqueous phase containing an water-soluble oxidizing to decompose the thiocyanate ion; and (g) recycling the organic phase thus obtained as the organic phase to step (d).

In the above described process, steps (e) and (f) can be conducted under the same conditions by the same procedure as in the treatment of the quaternary onium salt of formula [I].

The amount of the quaternary onium salt used in step (d) of the above described process mainly depends on that of $Rf'CO_2^-$ in a waste water phase. Usually the quaternary onium salt is employed in an amount of from 0.5 to 20 moles, preferably from 1 to 10 moles, more preferably from 1 to 5, per mole of $Rf'CO_2^-$. When the amount of the quaternary onium salt is less than 0.5 mole per mole of $Rf'CO_2^-$, the ratio of extraction of $Rf'CO_2^-$ is too small for practical purposes, whereas when the amount is greater than 20 moles per mole of $Rf'CO_2^-$, the operational cost of the process increases, which is disadvantageous from an economical standpoint.

The temperature and the device for carrying out step (d) which can be employed in this process are the same as in the above described ion exchange reaction by contacting an organic phase containing the quaternary onium salt of formula [I] with an aqueous phase containing $SCN^-$.

Figure 2:
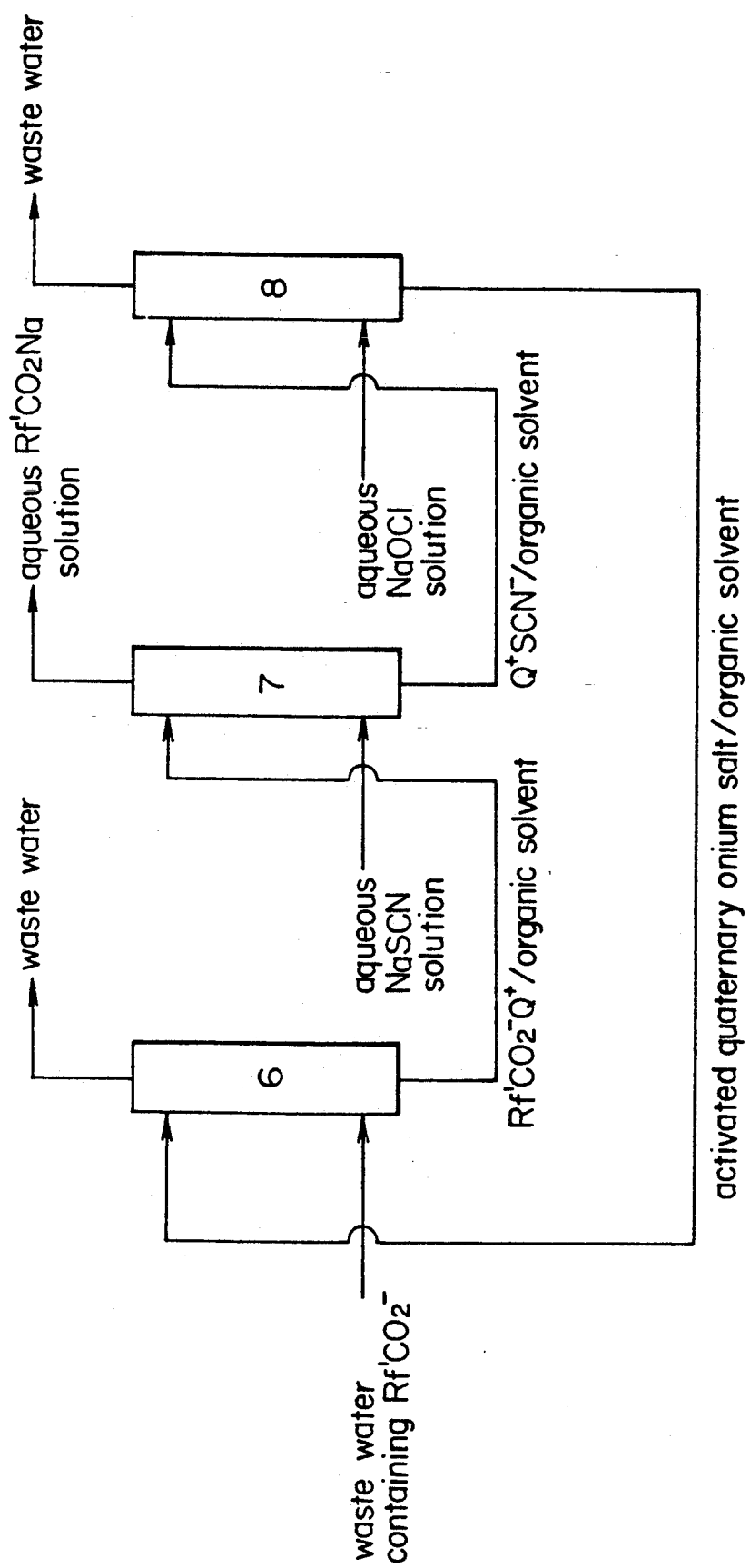
FIG. 2 and 3 are examples of block flow diagrams illustrating a process for removing a fluorine-containing carboxylate as a by-product from the aqueous phase in the preparation of hexafluoropropylene oxide from hexafluoropropylene.

With reference to FIG. 2, one embodiment of the process for the removal of the $Rf'CO_2^-$ from a waste water containing $Rf'CO_2^-$ will be explained.

In FIG. 2, numeral 6 is an ion exchange stern) where a waste water containing $Rf'COO^-$ after the preparation of HFPO is contacted with an organic solvent sparingly miscible in water containing, for example, tri-n-octylmethylammonium chloride as a quaternary ammonium salt or a quaternary phosphonium salt to conduct the ion exchange between the quaternary ammonium salt or the quaternary phosphonium salt and $Rf'CO_2^-$ and as a result, $Rf'CO_2^-$ is extracted from the aqueous phase to form $Rf'CO_2^-Q^+$ in the organic solvent phase. The aqueous phase thus obtained is discharged as a waste water. Numeral 7 is an ion exchange step where $Rf'CO_2^-Q^+$ in the organic solvent phase from step 6 is contacted with for example, an aqueous NaSCN solution as an aqueous phase containing $SCN^-$ to conduct the ion exchange between $Rf'CO_2^-Q^+$ and $SCN^-$ and as a result, $Rf'CO_2^-$ as $Rf'CO_2^-Na^+$ migrates to the aqueous phase while $Q^+SCN^-$ is formed in the organic solvent phase. Then the aqueous $Rf'CO_2^-Na^+$ solution is collected. Numeral 8 is a $SCN^-$ decomposition step where $Q^+SCN^-$ in the organic solvent phase is contacted with, for example, an aqueous NaOCl solution as an aqueous phase containing a water-soluble oxidizing agent to conduct the decomposition of $SCN^-$ in $Q^+SCN^-$ and as a result, in the organic solvent phase is formed an activated tri-n-octylmethylammonium salt as an activated quaternary ammonium salt or an activated quaternary phosphonium salt and this organic solvent phase is recycled to step 6 to extract $Rf'CO_2^-$. On the other hand, the aqueous phase is discharged as a waste water.

In carrying out the above described procedure the extraction of $R'CO_2^-$ and the recovery of $Rf'CO_2^-$ can be simultaneously effected.

Usually in the waste water phase containing $Rf'CO_2^-$ after the preparation of HFPO there remains a hypochlorite salt. Accordingly, when the hypochlorite salt is present in the waste water in an amount of the residual hypochlorite salt of at least 1 mole, preferably 2 to 100 moles, particularly preferably 2 to 20 moles per mole of the quaternary onium salt to be employed, the above described step 8 can be deleted. More specifically, the activation of the quaternary onium salt by the decomposition of $SCN^-$ and the extraction of $Rf'CO_2^-$ by the activated quaternary onium salt can be simultaneously conducted.

Figure 3:
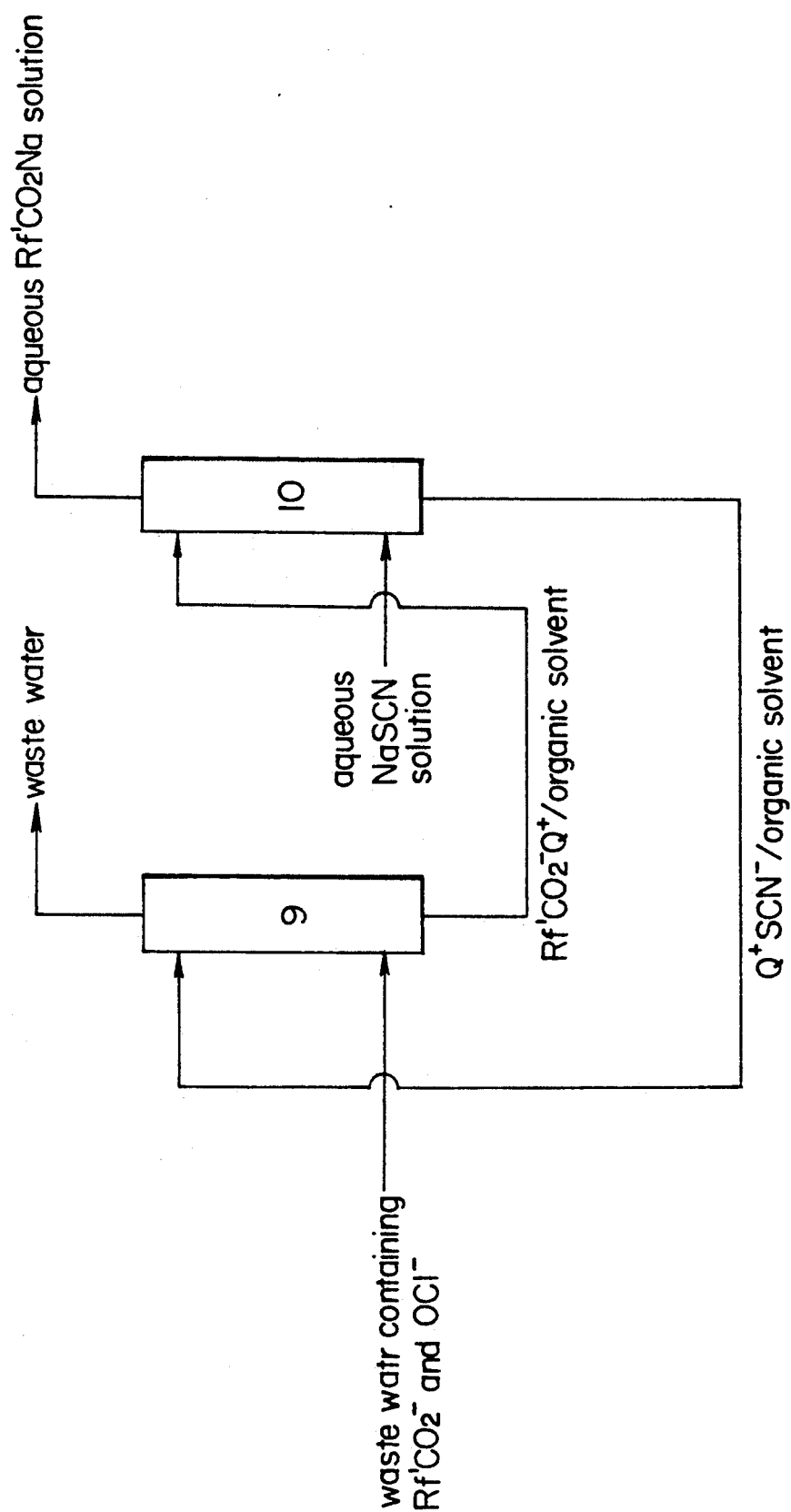

With reference to FIG. 3, one embodiment of this procedure will be explained. Numeral 9 is a step for the SCN$^-$ decomposition reaction and the ion exchange reaction. In step 9 the waste water containing RfCO$_2^-$ and OCl$^-$ is contacted with the organic solvent phase containing Q$^+$SCN$^-$ to form RfCO$_2^-$Q$^+$ by the decomposition of SCN$^-$ and the successive ion exchange reaction of the quaternary onium salt with RfCO$_2^-$, and the aqueous phase thus obtained is discharged as a waste water. Numeral 10 is a step for the ion exchange reaction where the organic solvent phase containing RfCO$_2^-$Q$^+$ from step 9 is contacted with, for example, an aqueous NASCN solution as an aqueous phase containing SCN$^-$. As a result, in the organic solvent phase is formed Q$^+$SCN$^-$ which is then recycled to step 9. On the other hand, the aqueous RfCO$_2^-$Na$^+$ solution is collected. Thus, by alternatingly repeating step 9 and step 10, the quaternary onium salt can repeatedly be used for the extraction of RfCO$_2^-$.

The procedure as described in FIG. 3 is more advantageous than that as described in FIG. 2 from the following viewpoints, ① one step can be deleted;

② the cost of a water-soluble oxidizing agent for the decomposition of SCH$^-$ is not required; and ③ the hypochlorite salt in the waste water phase is used for the reaction with SCN$^-$ to delete the reduction or decomposition treatment of the hypochlorite salt in the waste water phase.

[C] Activation of the catalyst and treatment of the waste water phase at the same time in the preparation of HFPO As shown in [B], the activation of the quaternary onium salt by the decomposition of SCN$^-$ and the extraction of RfCO$_2^-$ can be simultaneously carried out by treating the organic phase containing Q$^+$SCN$^-$ with a waste water phase containing a hypochlorite ion and RfCO$_2^-$ whose main component is CF$_3$CO$_2^-$.

It has been found that the quaternary onium salt whose main component is CF$_3$CO$_2^-$Q$^+$ obtained by the above described treatment shows a sufficient catalytic activity as the catalyst for the preparation of HFPO from HFP, in contrast with the quaternary onium salt whose main component is CF$_3$CFXCO$_2^-$Q$^+$ wherein X is F, Cl or H in the organic phase after the preparation of HFPO which requires an activation treatment. Such a difference in catalytic activity is not clear but it can be assumed that with respect to CF$_3$CO$_2^-$Q$^+$, an active ion pair of Q$^+$OCl$^-$ tends to form by more easily ion exchanging CF$_3$CO$_2^-$ with OCl$^-$ than CF$_3$CFXCO$_2^-$ since the stability of an ion pair of CF$_3$CO$_2^-$Q$^+$ is lower than that of an ion pair of CF$_3$CFXCO$_2^-$Q$^+$.

Thus, in the preparation of HFPO according to the process as described in [A], it is possible to employ the waste water phase containing unreacted hypochlorite salt formed in the preparation of HFPO as the aqueous solution containing a water-soluble oxidizing agent in step (b). In this process the mole number of the hypochlorite ion in the waste water before carrying out this treatment which can be employed is typically more than that of Q$^+$SCN$^-$ in the organic phase in step (b), preferably 2 to 100 times that of Q$^+$SCN. For practical purposes it is particularly preferred that the mole number of the hypochlorite ion is 3 to 15 times that of Q$^+$SCN$^-$.

In the preparation of +HFPO comprising a step of activating the quaternary onium salt with such a waste water phase, the RfCO$_2^-$ extracted from the waste water phase is recycled to the step of preparing HFPO from HFP, and with increased numbers of recycling, the amount of the RfCO$_2^-$ in the waste water phase increases and finally all of the RfCO$_2^-$ cannot be extracted with the quaternary onium salt catalyst. As a result, HFPO cannot be continuously prepared for a long period of time. Naturally, when the mole number of the RfCO$_2^-$ in the waste water phase is more than that of the quaternary onium salt catalyst in the organic phase, the RfCO$_2^-$ in the aqueous phase cannot be extracted.

It has been found that the above described problem can be solved by treating the waste water phase with Q$^+$SCN$^-$ whose mole number employed is more than the necessary mole number as the catalyst. More specifically, there is provided a process for preparing HFPO from HFP according to the process as described in [A] which comprises the steps of:

(h) contacting the organic phase containing a quaternary onium thiocyanate with the waste water phase containing unreacted hypochlorite and a by-produced fluorine-containing carboxylate formed in the step of preparing HFPO from HFP as the aqueous solution containing a water-soluble oxidizing agent in step (b); and (i) dividing the organic phase obtained into two portions and returning one portion of the organic phase to the step of preparing HFPO from HFP and recycling the other portion of the organic phase to step (a) to be contacted with the aqueous phase containing a thiocyanate ion.

In this process the mole number of the quaternary onium salt in the organic phase to be returned to step (a) is appropriately determined depending on the mole number of RfCO$_2^-$ in the waste water phase, the mole number of the quaternary onium salt in the organic phase used in the step of preparing HFPO from HFP, the HFP conversion and the HFPO selectivity obtained and the conditions for extracting RfCO$_2^-$ employed. Usually the process is conducted in such a manner that the total mole number of the quaternary onium salt to be used in the step of preparing HFPO from HFP and the quaternary onium salt in the organic phase to be recycled to step (a), i.e., the mole number of the quaternary onium salts used in steps (a) and (b) is from 5% by mole to 100% by mole, preferably from 10% by mole to 60% by mole of HFPO forming in the step of preparing HFPO from HFP. When the mole number of the quaternary onium salts used in steps (a) and (b) is too low in this process for preparing HFPO from HFP, the extraction of RfCO$_2^-$ from the aqueous phase is not sufficient. On the other hand, when the mole number is too high, the cost for conducting the process unfavorably becomes high. Further, the mole number of the hypochlorite ion in the aqueous phase as a waste water phase from the step of preparing HFPO from HFP which can be employed in this process is typically more than that of Q$^+$SCN$^-$ in step (a) and is preferably from 2 to 100 times that of Q$^+$SCN$^-$ in step (a). For practical purposes it is particularly preferred that the mole number of the hypochlorite ion is from 2 to 20 times that of Q$^+$SCN$^-$ in step (a).

Figure 4:
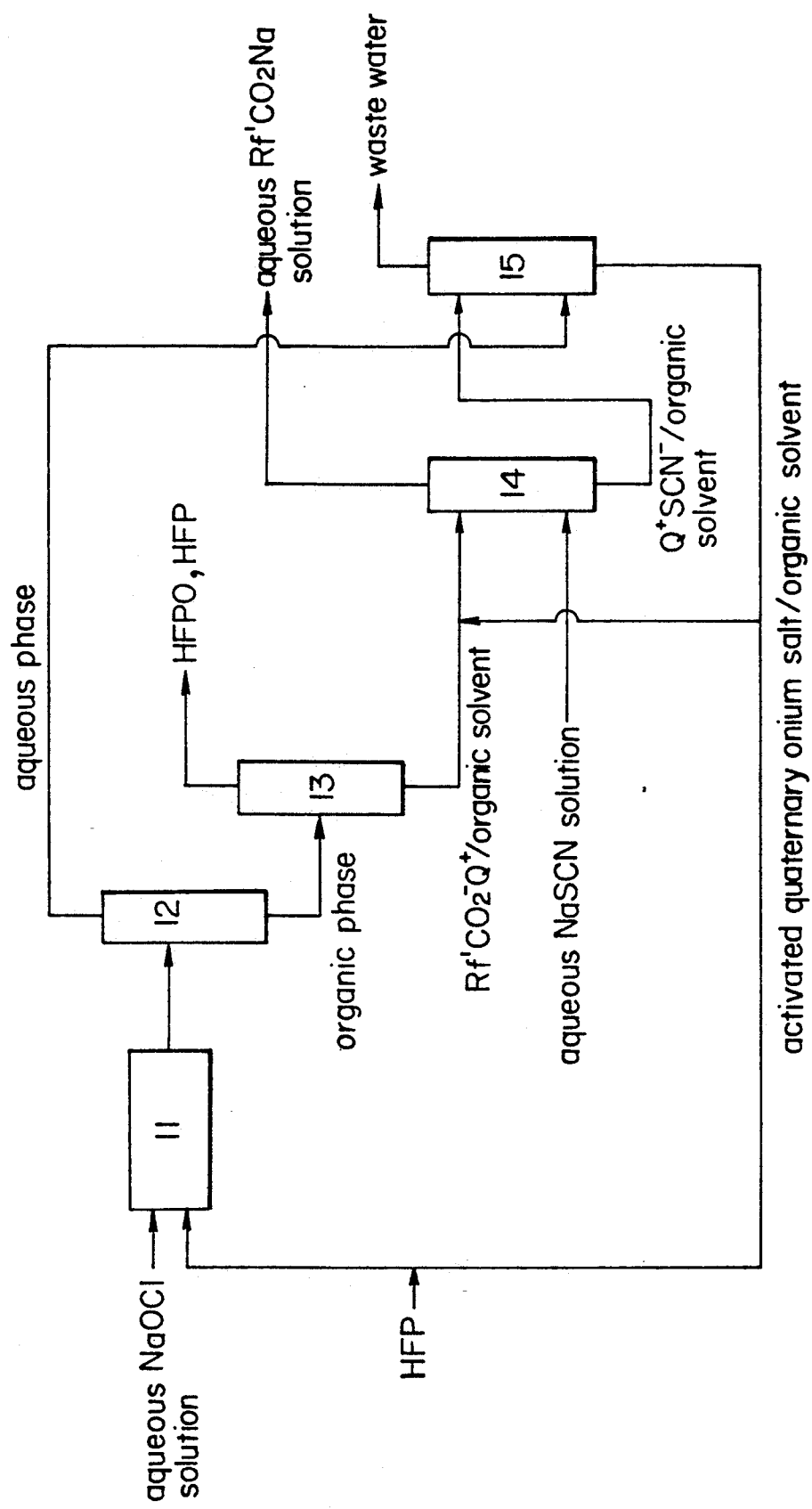
FIG. 4 is one example of block flow diagram illustrating a process for preparing hexafluoropylene oxide from hexafluoropropylene which comprises a step of activating a quaternary onium salt and removing a by-produced fluorine-containing carboxylate from a waste water phase at the same time.

With reference to FIG. 4 one embodiment of the above described process will be explained.

Steps 11, 12 and 13 are the same as steps 1, 2 and 3 in FIG. 1. Numeral 14 is a step for the ion exchange reaction and numeral 15 is a step for the decomposition of SCN⁻ and the ion exchange reaction. In step 14 the organic phase containing $R_fCO_2^-Q^+$ in which the main component of $R_fCO_2^-$ is $CF_3CFXCO_2^-Q^+$ wherein X is F, Cl or H from step 13 is combined with part of the organic phase from step 15 and the organic phase thus combined is contacted with an aqueous solution containing SCN⁻, for example, an aqueous NASCN solution to form an organic phase containing $Q^+SCN^-$. Then in step 15 the organic phase containing $Q^+SCN^-$ from step 14 is contacted with a waste water phase containing $R_fCO_2Na$ whose main component is $CF_3CO_2Na$ and NaOCl from step 12 to simultaneously conduct the activation of the quaternary onium salt by the decomposition of SCN⁻ and the extraction of $R_fCO_2^-$. The activated quaternary onium salt contains $R_fCO_2^-Q^+$ and $Q^+X^-$ and the main component of $R_fCO_2^-Q^+$ is $CF_3CO_2^-Q^+$ and $X^-$ in $Q^+X^-$ is not clear but seems to be OCl⁻. The organic phase from step 15 is divided into two portions and one portion is reused as an organic phase in step 11 for the preparation of HFPO, and the other portion is recycled to step 14. On the other hand, the aqueous phase from step 15 is discharged as a waste water.

In conducting the above described procedure substantially all of the amount of $R_fCO_2^-$ by-produced in step 11 for the preparation of HFPO can be separated as an aqueous solution of $R_fCO_2^-$ Na in step 12 and accordingly, the concentration of $R_fCO_2^-$ in the waste water phase from step 11 can be maintained constant. Thus, according to the above described process for the preparation of HFPO it is possible to stably and continuously conduct the preparation of HFPO for a long period of time as well as to conduct the activation of the catalyst, the separation of $R_fCO_2^-$ from the waste water phase and the decomposition of a hypochlorite ion in the waste water at the same time.

The following Examples and Comparative Examples are given to illustrate the present invention in greater detail although the present invention is not limited thereto.

Example 1

A 500 ml egg plant type flask equipped with a stirrer was charged with 100 ml of 1,1,2-trichloro-1,2,2-trifluoroethane (hereinafter referred to as "F-113") solution containing 4.0 g (10 millimoles) of tri-n-octylmethylammonium chloride (hereinafter referred to as "TOMAC") and 100 ml of an aqueous solution containing 2.04 g (15 millimoles) of sodium trifluoroacetate.

These solutions were vigorously stirred at 30° C. for 10 minutes. Thereafter, stirring was stopped and the mixture was left to stand to separate into an organic phase and an aqueous phase. The contents of the organic phase were analyzed by infrared absorption spectrocopy and ¹⁹F-NMR spectroscopy. As a result, it was found that almost all of the chlorine ion in the starting TOMAC was exchanged with $CF_3CO_2^+$ ion to form $CF_3CO_2^-Q^+$ wherein $Q^+$ was a tri-n-octylmethylammonium cation.

Infrared Absorption Spectrum $\nu_{c=O}$: 1695 cm⁻1 ($CF_3CO_2^-$)

$\nu_{c=H}$: 2940 cm⁻1 ($Q^+$)

¹⁹F-NMR Spectrum $CF_3$: 87 ppm (hexafluorobenzene standard) ($CF_3CO_2^-$)

Example 2

100 ml of the F-113 solution containing 10 millimoles of $CF_3CO_2^-Q^+$ as obtained in Example 1 and 100 ml of an aqueous solution containing 1.62 g (20 millimoles) of sodium thiocyanate were placed in a 500 ml egg plant type flask equipped with a stirrer and stirred at 30° C. for 10 minutes and stirring was stopped and the flask was left to stand to effect the phase separation of an organic phase and an aqueous phase. When the contents of the organic phase were analyzed by infrared absorption spectroscopy and ¹⁹F-NMR spectroscopy, 91% of the $CF_3CO_3^-$ in $CF_3CO_2^-Q^+$ were converted to SCN⁻.

Infrared Absorption Spectrum $\nu_{c=O}$: 1695 cm⁻1 (residual $CF_3CO_2^-Q^+$)

$\nu_{SCN}$: 2050 cm⁻1 (SCN⁻)

$\nu_{c-H}$: 2940 cm⁻1 ($Q^+$)

¹⁹F-NMR Spectrum $CF_3$: 87 ppm (hexafluorobenzene standard) ($CF_3CO_2^-Q^+$)

Comparative Example 1

The procedure of Example 2 was repeated with the exception that 20 millimoles of sodium chloride were used instead of the sodium thiocyanate. As a result, hardly any conversion of $CF_3CO_2^-Q^+$ to $Q^+Cl^-$ was observed.

Example 3

The ion exchange reaction between $CF_3CO_2^-Q^+$ in an organic phase and sodium thiocyanate in an aqueous phase was conducted using a jacketed multistage counter current extracting column having a column diameter of 40 mm and 10 stage stirring compartments.

The same F-113 solution of $CF_3CO_2^-Q^+$ as in Example 2 and an aqueous NASCN solution at a mole ratio of $CF_3CO_2^-Q^+$ to NASCN being 1 to 1.5 were contacted in the above described equipment at a jacket temperature of 15° C. As a result, almost all of the amount of the $CF_3CO_2^-$ in $CF_3CO_2^-Q^+$ in the organic phase was converted to SCN⁻.

Example 4

In a 300 ml egg plant type flask equipped with a stirrer were placed 100 ml of F-113 solution containing 10 millimoles of tri-n-octylmethylammonium thiocyanate (hereinafter referred to as "TCA") and an aqueous solution containing 1N sodium hypochlorite by varying the mole ratio of tri-n-octylmethylammonium thiocyanate to sodium hypochlorite, and the solution was vigorously stirred at 20° C. for 10 minutes. Then, stirring was stopped and the mixture was left to stand to separate into an organic phase and an aqueous phase. The contents of the organic phase were analyzed by infrared absorption spectroscopy. The results are shown in Table 1 below.

TABLE 1

| Run No. | NaOCl/TCA (mole ratio) | Decomposition Ratio of SCN⁻ in TCA (%) |
|---|---|---|
| 1 | 2.2 | 56 |
| 2 | 3.2 | 81 |
| 3 | 4.3 | 92 |
| 4 | 5.4 | 100 |

As is clear from Table 1, the decomposition of the SCN⁻ in tri-n-octylmethylammonium thiocyanate was confirmed.

Also, it was confirmed by the ¹H-NMR spectrum of the organic phase that any Q⁺ in the organic phase was not decomposed in the above described procedure. Further, it was confirmed that any SCN⁻ did not exist in the aqueous phase.

Furthermore, the procedure of Example 1 was repeated except that the organic phase as obtained in the above described Run No. 4 was employed instead of the F-113 solution of Q⁺Cl⁻. As a result, almost all of the quaternary ammonium salt in the organic phase was converted to $CF_3CO_2^-Q^+$. This shows that an easily ion exchangeable active quaternary ammonium salt like Q⁺Cl⁻ was formed in an organic phase by treating an organic phase containing tri-n-octylmethylammonium thiocyanate with an aqueous phase containing sodium hypochlorite.

comparative Example 2

In the same manner as in Example 4, 100 ml of an F-113 solution containing 10 millimoles of tri-n-octylmethylammonium thiocyanate and 100 ml of an aqueous solution containing 50 millimoles of sodium chloride were stirred. As a result, the SCN⁻ of tri-n-octylmethylammonium thiocyanate in the organic phase was hardly decreased.

Example 5

In the same manner as in Example 1 the F-113 solution of Q⁺Cl⁻ was contacted with each of the aqueous solutions of various sodium fluorocarboxylates to obtain an F-113 solution of $CF_3CF_2CO_2^-Q^+$, $CF_3CFHCO_2^-Q^+$ or $CF_3CFClCO_2^-Q^+$. Each of these F-113 solutions was treated with an aqueous NASCN solution in the same manner as in Example 3 to convert $RfCO_2^-Q^+$ to tri-n-octylmethylammonium thiocyanate. The results are shown in Table 2.

TABLE 2

| $RfCO_2^-Q^+$ | Conversion to TCA (%) |
| --- | --- |
| $CF_3CF_2CO_2^-Q^+$ | 94 |
| $CF_3CFHCO_2^-Q^+$ | 96 |
| $CF_3CFClCO_2^-Q^+$ | 94 |

Example 6

The conversions of various $RfCO_2^-Q^+$ as shown in Table 3 below to tri-n-octylmethylammonium thiocyanate were conducted by repeating the procedure of Example 5 except that hetrachloroethane was employed instead of the F-113 and the mole ratio of NASCN to $RfCO_2^-Q^+$ of 3 to 1 was employed instead of that of 1.5 to 1. The results are shown in Table 3.

TABLE 3

| $RfCO_2^-Q^+$ | Conversion to TCA (%) |
| --- | --- |
| $CF_3(CF_2)_2CO_2^-Q^+$ | 97 |
| $CF_3(CF_2)_4CO_2^-Q^+$ | 95 |
| $CF_3(CF_2)_6CO_2^-Q^+$ | 91 |
| $H(CF_2)_7CO_2^-Q^+$ | 90 |
| $CF_3CF_2CF_2OCF(CF_3)CO_2^-Q^+$ | 95 |

Example 7

The decomposition of the SCN⁻ of tri-n-octylmethylammonium thiocyanate was conducted by repeating the procedure of Example 4 except that each of various water-soluble oxidizing agents as shown in Table 4 below was employed instead of the sodium hypochlorite and the mole ratio of the oxidizing agent to tri-n-octyl-methylammonium thiocyanate employed was 1 to 10 and the stirring was conducted at 30° C. for 20 minutes. The concentration of the water-soluble oxidizing agents as shown in Table 4 was 2N.

The results are shown in Table 4. All of the water-soluble oxidizing agents were effective for the decomposition of the SCN⁻. Also, all of the quaternary ammonium salts in the organic phase obtained by this treatment exhibited good extractability of $CF_3CO_2^-$ to show the formation of ion exchangeable active quaternary ammonium salts as in Example 4.

TABLE 4

| Water-Soluble Oxidizing Agent | Decomposition Ratio of SCN⁻ of TCA (%) |
| --- | --- |
| NaOCl | 100 |
| $H_2O_2$ | 96 |
| $HNO_3$ | 100 |
| $Cl_2$ (Chlorine water) | 100 |

Example 8

The decomposition of the SCN⁻ of tri-n-octylmethylammonium thiocyanate by various water-soluble oxidizing agents as shown in Table 5 below was conducted by repeating the procedure of Example 7 except that tetrachlorocarbon was employed as an organic solvent instead of the F-113 and the mole ratio of each of the water-soluble oxidizing agents to tri-n-octylmethylammonium thiocyanate and the stirring time (i.e., oxidation treatment time) as shown in Table 5 were employed.

The results are shown in Table 5. All of the water-soluble oxidizing agents employed were effective for the decomposition of the SCN⁻. Also, all of the quaternary ammonium salts in the organic phase obtained by this treatment exhibited good extractability of $CF_3CO_2^-$ as in Example 4 to show the formation of ion exchangeable active quaternary ammonium salts.

TABLE 5

| Water-Soluble Oxidizing Agent | Ratio of Water-Soluble Oxidizing Agent to Q⁺SCN⁻ (mole ratio) | Stirring Time (hour) | Decomposition Ratio of SCN⁻ of TCA (%) |
| --- | --- | --- | --- |
| NaOCl | 10 | 0.5 | 100 |
| $H_2O_2$ | 10 | 0.5 | 96 |
| $HNO_3$ | 10 | 0.5 | 98 |
| $NaClO_3$ | 20 | 1.0 | 93 |
| $NaNO_3$ | 15 | 1.0 | 95 |
| $Ca(OCl)_2$ | 15 | 1.0 | 97 |
| HOCl* | 10 | 0.5 | 98 |
| $(CH_3)_3COOH$ | 10 | 1.0 | 95 |

*an aqueous solution having a pH of 2.8 prepared by adding concentrated hydrochloric acid to an aqueous 2N NaOCl solution

Example 9

The procedure of Example 5 was repeated except that dichloroethane was employed as an organic solvent instead of the F-113 and various onium trifluoroacetates as shown in Table 6 below were employed instead of $RfCO_2^-Q^+$.

The dichloroethane solution of each of these onium trifluoroacetates was treated with an aqueous NASCN solution for the conversion to onium thiocyanates. The results are shown in Table 6 below.

Further, when the dichloroethane solution of each of the onium thiocyanates obtained by the above described treatment was treated with an aqueous sodium hypochlorite solution under the same conditions as in Example 7, the SCN− of the onium thiocyanates was completely decomposed.

TABLE 6

| Onium Trifluoroacetate | Conversion to Onium Thiocyanate (%) |
|---|---|
| $CF_3CO_2^{-+}N(n\text{-butyl})_4$ | 100 |
| $CF_3CO_2^{-+}N(n\text{-octyl})_4$ | 100 |
| $CF_3CO_2^{-+}N(C_2H_5)_3(CH_2\text{—}\langle\text{Ph}\rangle)$ | 99 |
| $CF_3CO_2^{-+}N(n\text{-decyl})_4$ | 98 |
| $CF_3CO_2^{-+}P(n\text{-octyl})_3(CH_3)$ | ≈100 |
| $CF_3CO_2^{-+}P(\langle\text{Ph}\rangle)_3(CH_2\text{—}\langle\text{Ph}\rangle)$ | 98 |
| $CF_3CO_2^{-+}P(n\text{-butyl})_4$ | ≈100 |

Example 10

The decomposition of the SCN− of tri-n-octylmethylammonium thiocyanate was conducted by repeating the procedure of Example 4 except that an aqueous 0.3N sodium persulfate solution was employed instead of the aqueous 1N sodium hypochlorite solution, the mole ratio of sodium persulfate to tri-n-octylinethylammonium thiocyanate employed was 3.0 to 1.0 and stirring was carried out at 40° C. for 30 minutes. As a result,, 73% of the SCN− were decomposed.

Example 11

Preparation of Hexafluoropropylene Oxide

A 300 ml pressure resistant glass reactor equipped with a fluorine resin-coated stirring bar, a pressure gauge, a nozzle for a thermocouple, a cooling device, a nozzle (A) for sampling and a nozzle (B) for supplying a reaction solution and withdrawing a reaction product was charged with 160 ml of an F-113 solution containing 0.580 g (1.44 millimoles) of TOMAC and 70 ml of an aqueous sodium hypochlorite solution with an available chlorine content of 6% containing 1.5% by weight of sodium hydroxide. After the contents of the reactor were cooled to −5° C., 4.20 g of hexafluoropropylene cooled to −5° C. were charged in the reactor and the reactants were vigorously stirred to initiate reaction. During the reaction, the reactor was cooled so as to maintain the temperature of the reaction solution at a temperature of −5° C. to −3° C.

One minute, two minutes, five minutes and ten minutes after the start of the reaction, stirring was stopped to withdraw the reaction product from the reactor for quantitative analysis by gas chromatography, respectively. As a result, the selectivity of hexafluoropropylene oxide was about 80% at the respective reaction time.

The respective conversions of hexafluoropropylene are shown in Table 7 below, and the reaction was completed in ten minutes.

After completion of the 10 minute reaction, the pressure within the reactor was reduced and hexafluoropropylene oxide and about 40 ml of F-113 were removed from the reactor through nozzle (B). Then, the pressure within the reactor was rendered atmospheric and the aqueous phase was removed from nozzle (B) and 70 ml of an aqueous sodium hypochlorite solution with an available chlorine content of 6% containing 1.5% by weight of sodium hydroxide and F-113 in the same amount as removed under reduced pressure were charged in the reactor through nozzle (B). Then the reactor was sealed and the contents of the reactor were cooled to −5° C. and 4.20 g of hexafluoropropylene cooled to −5° C. were charged in the reactor. The subsequent procedure for the preparation of hexafluoropropylene oxide was conducted in the same manner as in the first preparation of hexafluoropropylene oxide.

The above described procedure was repeated 20 times. The results of the twentieth reaction are also shown in Table 7.

TABLE 7

| Reaction No. | HFP Conversion (%) | | | |
|---|---|---|---|---|
| | after 1 minute | after 2 minutes | after 5 minutes | after 10 minutes |
| First Reaction | 62 | 81 | 96 | ≈100 |
| Twentieth Reaction | 19 | 36 | 67 | 88 |

As is shown in Table 7, the rate of reaction in the twentieth reaction was decreased compared to that in the first reaction. Accordingly, the structure of the onium catalyst in the F-113 solution after the twentieth reaction was investigated to obtain the following results.

<Infrared Absorption Spectrum>

A specific absorption band of a fluorine-containing carboxylate anion was observed at 1695 cm$^{-1}$.

<$^1$H-NMR Spectrum>

No change in Q+(tri-n-octylmethylammonium cation) was confirmed.

<$^{19}$F-NMR Spectrum>

The signals as shown below were observed and the presence of fluorine-containing carboxylate anions such as $CF_3CFXCO_2^-$ wherein X is F, Cl or H, and $CF_3CO_2^-$ at a mole ratio of $CF_3CFXCO_2^-$ to $CF_3CO_2^-$ of 85 to 15 was suggested from the comparison of the $^{19}$F-NMR spectrum of an authentic sample.

Chemical Shift from Hexafluorobenzene (ppm)

$$\underset{79.1}{CF_3}\text{—}\underset{40.1}{CF_2}\text{—}CO_2^-, \quad \underset{82.6}{CF_3}\text{—}\underset{30.6}{CFCl}\text{—}CO_2^-$$

$$\underset{86.4}{CF_3}\text{—}\underset{-41.6}{CFH}\text{—}CO_2^-, \quad \underset{86.2}{CF_3}\text{—}CO_2^-$$

From the above described results, it was found that most of the TOMAC (Q+Cl−) used as a catalyst in the first reaction was changed to a quaternary ammonium salt of RfCO$_2^-$Q+ after the twentieth reaction. The RfCO$_2^-$ in RfCO$_2^-$Q+ are fluorine-containing carboxylate anions having 2 or 3 carbon atoms and are considered as by-products derived from HFPO formed or HFP in the preparation of HFPO.

The reason that the catalytic activity of $RfCO_2^-Q^+$ is lower than that of $Q^+Cl^-$ seems due to the formation of a stable ion pair of $RfCO_2^-$ and $Q^+$ and in the preparation of HFPO the ion exchange between the $RfCO_2^-$ in $RfCO_2^-Q^+$ and $OCl^-$ in the aqueous phase is difficult to occur and as a result, $Q^+OCl^-$ as an active species for the epoxidation of HFP to HFPO might be hard to form in the preparation of HFPO.

In fact, when the F-113 solution containing $RfCO_2^-Q^+$ was stirred with an aqueous solution containing sodium hypochlorite or sodium chloride in an amount by mole five times the amount of $RfCO_2^-Q^+$, hardly any ion exchange from $RfCO_2^-Q^+$ to $Q^+OCl^-$ or $Q^+Cl^-$ occurred.

Example 12

Activation of Catalyst with Decreased Catalytic Activity

In the same manner as in Example 2, using 20 ml of an aqueous 5% by weight NASCN solution the ion exchange treatment was conducted with 160 ml of the F-113 solution containing 1.44 millimoles of the quaternary ammonium salt catalyst with decreased catalytic activity containing at least 90% by mole of $RfCO_2^-Q^+$ in the quaternary ammonium salt catalyst as obtained in Example 11. After the treatment, about 70% by mole of $RfCO_2^-$ in $RfCO_2^-Q^+$ were exchanged with $SCN^-$. After repeating the ion exchange treatment five times almost all of the quaternary onium salts in the F-113 solution were converted to $Q^+SCN^-$.

In a 300 ml egg plant type flask equipped with a stirrer were charged the entire F-113 phase containing the $Q^+SCN^-$ formed in the above described procedure and 20 ml of an aqueous sodium hypochlorite solution with an available chlorine content of 6% containing 1.5% by weight of sodium hydroxide, and the contents of the flask were stirred at a bath temperature of 30° C. for 15 minutes. As a result, it was confirmed by the analysis of the infrared absorption spectrum that all of the $SCN^-$ in $Q^+SCN^-$ in the F-113 phase was decomposed as in Example 4.

Example 13

Preparation of HFPO with Activated Catalyst

The procedure for preparing HFPO of Example 11 was repeated except that 160 ml of the F-113 solution containing 1.44 millimoles of the quarternary ammonium salt catalyst as obtained in Example 12 were employed instead of 160 ml of the F-113 solution containing 1.44 millimoles of TOMAC. The results are shown in Table 8. It was confirmed that the catalytic activity of the activated catalyst of Example 12 was almost same as that of TOMAC.

TABLE 8

| | HFP conversion (%) | | |
|---|---|---|---|
| after 1 minute | after 2 minutes | after 5 minutes | after 10 minutes |
| 64 | 82 | 96 | ≈100 |

Example 14

Continuous Preparation of HFPO

Figure 5:
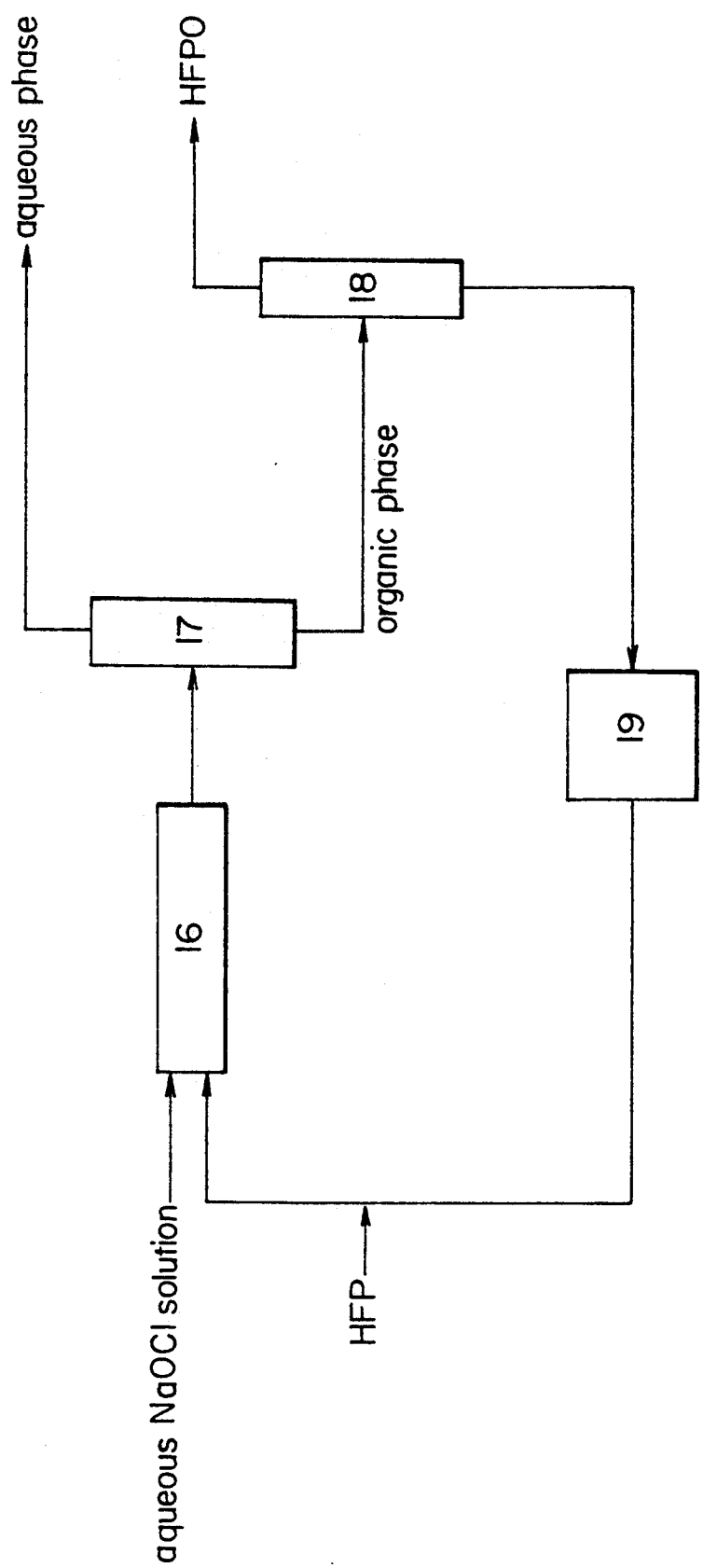
FIG. 5 is one example of block flow diagram illustrating a process for continuously preparing hexafluoropropylene oxide from hexafluoropropylene by repeatedly using a quaternary onium salt catalyst.

Using of continuous reaction equipment as shown in FIG. 5, comprising a 1.2 l tubular reactor 16, a decanter 17, a HFPO distillation column 18 and a 5 l organic phase tank 19, HFPO was continuously prepared from HFP.

The tubular reactor 16 was cooled to −5° C. and a F-113 solution containing 1.2% by weight of TOMAC was circulated in the reaction equipment at a flow rate of 9.4 l per hour. Then, an aqueous sodium hypochlorite solution containing 1.0 mole per liter of sodium hypochlorite and 1.5% by weight of sodium hydroxide was introduced into the tubular reactor 16 at a flow rate of 8.2 l per hour, and HFP was introduced into an organic phase line before the tubular reactor 16 at a flow rate of 0.5 Kg per hour to start the reaction.

The reaction solution leaving the tubular reactor 16 was introduced into the decantor 17 where it was separated into an organic phase and an aqueous phase. The aqueous phase was discharged out of the reaction equipment, while the organic phase containing HFPO formed was sent to the HFPO distillation column 18 where HFPO formed and unreacted HFP were separated from the organic phase. The organic phase from which HFPO and HFP had been distilled in the HFPO distillation column 18 was sent to the organic phase tank 19 and, thereafter, was returned to the tubular reactor 16.

Fifteen minutes after the start of the reaction, the HFP conversion was over 99% and the HFPO selectivity was 81% by gas chromatography analysis. However, when the reaction was continued for 30 hours, the HFP conversion was decreased to 72%.

Example 15

The structure of the quaternary onium salt catalyst with decreased catalytic activity in the organic phase after the 30-hour continuous preparation of HFPO of Example 14 was examined in the same manner as in Example 11 and as a result, almost all of the quaternary onium salt catalyst was $RfCO_2^-Q^+$ and the mole ratio of $CF_3CFXCO_2^-$ wherein X was F or Cl to $CF_3CO_2^-$ in $RfCO_2^-$ was 84 to 16. The organic phase containing this quaternary onium salt catalyst with decreased catalytic activity was treated by the following method to activate the catalyst.

In the same multistage counter-current extracting column as used in Example 3, 6 l of the above described organic phase was counter-currently contacted with 8 l of an aqueous 2% by weight NASCN solution at a jacket temperature of 15° C. As a result, almost all of the quaternary onium salt was changed to $Q^+SCN^-$.

In a 10 l reactor were placed 6 l of the F-113 solution containing $Q^+SCN^-$ thus obtained, part of which was present in the form of a suspension, which was then slowly added, under stirring, with 3 l of an aqueous 1-N hypochlorite solution containing 1.5% by weight of sodium hydroxide at a temperature of at most 40° C. After completion of the addition of the aqueous 1N hypochlorite solution, stirring was continued at 40° C. for 15 minutes. Then, the contents of the organic phase were analyzed by infrared absorption spectroscopy to confirm the decomposition of all of the $SCN^-$ in $Q^+SCN^-$.

The preparation of HFPO from HFP of Example 14 was conducted using 5 l of the F-113 solution containing the quaternary onium salt thus obtained instead of the F-113 solution containing 1.2% by weight of TOMAC in such a manner that the aqueous phase was introduced into the continuous reaction equipment before the organic phase.

Fifteen minutes after the start of introducing HFP and the organic phase into the continuous reaction equipment, the reaction solution from tubular reactor 16 was analyzed by gas chromatography and as a result, the HFP convertion was at least 99% and the HFPO selectivity was 80%. From these results, it was confirmed that a catalyst showing the reaction results equivalent to those of TOMAC was formed by the above described activation of the catalyst with decreased catalytic activity.

Further, 160 ml of a F-113 solution containing 1.44 millimole of $Q^+SCN^-$ were prepared using the F-113 solution containing $Q^+SCN^-$ obtained during the above described procedure. Then, the procedure of Example 11 was repeated using the F-113 solution thus obtained, 100 ml of an aqueous sodium hypochlorite solution containing 1.5% by weight of sodium hydroxide with an available chlorine content of 6% and 4.20 g (28 millimoles) of HFP.

One minute, five minutes and ten minutes after the start of the reaction, the HFP conversions were 60% 93% and 100%, respectively and the HFPO selectivity was nearly 80% at the respective reaction times. Thus, the reaction results were similar to those obtained in the preparation of HFPO from HFP using $Q^+Cl^-$ of Example 11.

Example 16

The procedures of Examples 1, 3 and Run No. 4 of Example 4 were repeated except that n-hexane and toluene were employed instead of F-113 as the solvent, respectively. As a result, the conversions as shown below were nearly 100% in each case.

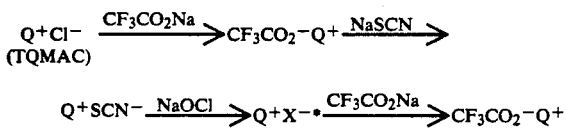

$$Q^+Cl^- \xrightarrow{CF_3CO_2Na} CF_3CO_2^-Q^+ \xrightarrow{NaSCN}$$
(TQMAC)

$$Q^+SCN^- \xrightarrow{NaOCl} Q^+X^{-*} \xrightarrow{CF_3CO_2Na} CF_3CO_2^-Q^+$$

*The structure of $X^-$ was not identified but $SCN^-$ was not present in $X^-$.

Example 17

The distribution of $RfCO_2^-$ in the aqueous phase as a waste water phase having a pH of 12.3 obtained in the period between one and three hours after the start of the continuous preparation of HFPO of Example 14 was analyzed by $^{19}$F-NMR spectroscopy. As a result, the mole ratio of $CF_3CO_2^-$ to $CF_3CFXCO_2^-$ wherein X was F or Cl was 87 to 13.

<Procedure A>

In the same multistage counter-current extracting column as used in Example 3, 5 l of the aqueous phase as a waste water phase as obtained above were counter-currently contacted with 10 l of a F113 solution containing 400 g of TOMAC at a jacket temperature of 20° C. As a result, almost all of the $RfCO_2^-$ in the aqueous phase was extracted in the organic phase to form $RfCO_2^-Q^+$.

<Procedure B>

Then, in the same multistage counter-current extracting column as used in Procedure A, 9 l of the organic phase containing $RfCO_2^-Q^+$ thus obtained were counter-currently contacted with 10 l of an aqueous solution containing 300 g of sodium thiocyanate at a jacket temperature of 20° C. As a result, almost all of the quaternary onium salt was changed to $Q^+SCN^-$.

<Procedure C>

Further, in the same multistage counter-current extracting column as used in Procedure A, 8 of the F-113 solution containing $Q^+SCN^-$ thus obtained were counter-currently contacted with 6 of an aqueous about 2N sodium hypochlorite solution with an available chlorine content of 12% at a jacket temperature of 20° C. As a result, it was confirmed by infrared absorption spectroscopy that all of the $SCN^-$ in $Q^+SCN^-$ in the organic phase was decomposed.

<Procedure D>

Furthermore, 3 l of the above described aqueous phase as a waste water phase containing $RfCO_2^-$ was treated with 6 l of the F-113 solution containing the quaternary onium salt obtained in Procedure C in the same manner as in Procedure A. As a result, almost all of the $RfCO_2^-$ in the aqueous phase was extracted in the organic phase.

This result shows that the quaternary onium salt obtained in Procedure C had the extractability of $RfCO_2^-$ equivalent to that of the TOMAC used in Procedure A.

Example 18

The procedure for the continuous preparation of HFPO of Example 14 was repeated except that the flow rate of the aqueous sodium hypochlorite solution was changed from 8.2 l per hour to 9.8 l per hour, and the flow rate of the F-113 solution containing TOMAC was changed from 9.4 l per hour to 7.5 l per hour, and the rate of feeding HFP was changed from 0.5 Kg per hour to 0.4 Kg per hour.

As a result, 30 minutes after the start of introducing HFP at the outlet of the tubular reactor, the HFP conversion was nearly 100% and the HFPO selectivity was 78%. Further, 5 hours after the start of introducing HFP, the HFP conversion was 96% and the HFPO selectivity was 81%. The mole ratio of $CF_2CO_2^-$ to $CF_3CFXCO_2^-$ wherein X was F or Cl in about 20 l of the aqueous phase as a waste water phase obtained in the period between 3 hours and 5 hours after the start of introducing HFP in the above described continuous preparation of HFPO was 88 to 12.

<Procedure E>

In the same multistage counter-current extracting column as used in Procedure A of Example 17, 12 l of a F-113 solution containing 0.045 mol per liter of $Q^+SCN^-$ were counter-currently contacted with 5.2 l of the above described aqueous phase at a jacket temperature of 20° C. As a result, $SCN^-$ in the organic phase completely disappeared and almost all of the $RfCO_2^-$ was extracted in the organic please to form $RfCO_2^-Q^+$.

<Procedure F>

In the same multistage counter-current extracting column as used in Procedure A of Example 17, 10 l of the organic phase containing $RfCO_2^-Q^+$ thus obtained were counter-currently contacted with 5 l of an aqueous solution containing 200 g of sodium thiocyanate at a jacket temperature of 20° C. As a result, almost all of the quaternary onium salt was changed to $Q^+SCN^-$ and $RfCO_2^-$ migrated to the aqueous phase.

<Procedure G>

Procedure E was repeated using the organic phase containing $Q^+SCN^-$ obtained in Procedure F. As a result, the $RfCO_2^-$ in the aqueous phase as a waste water phase was mostly extracted in the organic phase.

Example 19

The preparation of HFPO from HFP as illustrated in FIG. 4 in which the steps of activating the catalyst and treating the waste water phase were combined with the step of preparing HFPO in Example 18 was conducted.

<Procedure H (corresponding to step 15 in FIG. 4)>

In the same multistage counter-current extracting column as used in Example 3, 9.8 l of the waste water which were part of the waste water collected during the period between 3 hours and 5 hours after the start of the preparation of HFPO in Example 18, 9.8 l being corresponding to the amount of the waste water formed in one hour were counter-currently contacted with 22.5 l of the F-113 solution containing 0.045 mole per liter of $Q^+SCN^-$ and as a result, SCN completely disappeared in the organic phase and most of the $RfCO_2^-$ in the waste water phase was extracted in the organic phase to form $RfCO_2^-Q^+$.

<Procedure I (corresponding to steps 11, 12 and 13 in FIG. 4)>

The procedure of Example 18 was repeated except that 7.5 l of the organic phase containing $RfCO_2^-Q^+$ obtained in Procedure H were employed as the organic phase. As a result, 30 minutes after the start of the reaction the HFP conversion was at least about 99% and the HFPO selectivity was 81% at the outlet of the tubular reactor. This reaction results show that the quaternary onium salt catalyst obtained in Procedure H was more active than that obtained in Example 18 five hours after the continuous preparation of HFPO using the catalyst recycled.

<Procedure i (corresponding to step 14 in FIG. 4)>

There were mixed 7.5 l of the organic phase containing $RfCO_2^-Q^+$ obtained in Procedure H, 7.5 l being corresponding to the amount of the organic phase recycled to step 14 for 30 minutes and 3.75 l of the organic phase containing the quaternary onium catalyst with decreased catalytic activity obtained from the bottom of the HFPO distillation column for 30 minutes during the period between 5 hours and 5.5 hours after the start of the reaction in Example 18.

In the same multistage counter-current extracting column as used in Example 3, 11.25 l of the mixed solution thus obtained which were corresponding to the organic phase containing $RfCO_2^-Q^+$ to be recycled to step 14 for 30 minutes, were counter-currently contacted with 5 l of an aqueous solution containing 200 g of NaSCN. As a result, the quaternary onium salt in the organic phase was mostly converted to $Q^+SCN^-$.

Thus, these results shows that the process for the preparation of HFPO from HFP comprising steps of activating the catalyst and treating the waste water as typically shown in FIG. 4 can be continuously conducted.

What is claimed is:

1. A process for the treatment of a quaternary onium salt which comprises the steps of:

(i) contacting an organic phase sparingly miscible in water containing a quaternary onium fluorine-containing carboxylate represented by formula (I)

$$RfCO_2^{-+}AR^1R^2R^3R^4$$

wherein

A is a nitrogen atom or a phosphorus atom;

$R^1$, $R^2$, $R^3$ and $R^4$ may be the same or different and each is a hydrocarbon group which is unsubstituted or substituted by a functional group inert to the reaction conditions and may contain another onium ion, the total number of carbon atoms contained in $R^1$, $R^2$, $R^3$ and R4 being at least 8 per onium ion, and $R^1$ and $R^2$ or $R^1$, $R^2$, and $R^3$ or $R^1$, $R^2$, $R^3$, and $R^4$ may combine to form a heterocyclic ring; and $RfCO_2^-$ is a polyfluorocarboxylate anion having from 2 to 15 carbon atoms, with an aqueous phase containing a thiocyanate ion to form a quaternary onium thiocyanate in the organic phase and transfer said $RfCO_2^-$ to said aqueous phase; and (ii) contacting the organic phase containing the quaternary onium thiocyanate with an aqueous solution containing a water-soluble oxidizing agent to decompose a thiocyanate ion and to form an easily ion exchangeable quaternary onium salt in said organic phase.

2. A process as claimed in claim 1, wherein A in formula (I) is a phosphorus atom and the total number of carbon atoms contained in $R^1$, $R^2$, $R^3$, and $R^4$ is from 8 to 70 per quaternary phosphonium ion.

3. A process as claimed in claim 1, wherein the water-soluble oxidizing agent is hydrogen peroxide.

4. A process as claimed in claim 1, wherein the water-soluble oxidizing agent is nitric acid or sodium nitrate.

5. A process as claimed in claim 2, wherein $R^1$, $R^2$, $R^3$, and $R^4$ each is an alkyl group.

6. A process as claimed in claim 5, wherein $^+AR^1R^2R^3R^4$ is a tri-n-octylmethylammonium ion.

7. A process as claimed in claim 1, wherein $RfCO_2^-$ in formula [I] is a polyfluorocarboxylate anion having from 2 to 3 carbon atoms.

8. A process as claimed in claim 1, wherein the polyfluorocarboxylate anion is at least one anion selected from the group consisting of $CF_3CO_2^-$, $CF_3CF_2CO_2^-$, $CF_3CFClCO_2^-$ and $CF_3CFHCO_2^-$.

9. A process as claimed in claim 1, wherein A in formula [I] is a nitrogen atom and the total number of carbon atoms contained in $R^1$, $R^2$, $R^3$ and $R^4$ is from 8 to 70 per quaternary ammonium ion.

10. A process as claimed in claim 9 wherein $R^1$, $R^2$, $R^3$ and $R^4$ each is an alkyl group.

11. A process as claimed in claim 10, wherein $^+AR^1R^2R^3R^4$ is a tri-n-octylmethylammonium ion.

12. A process as claimed in claim 1, wherein the organic solvent forming the organic phase sparingly miscible in water is at least one solvent selected from the group consisting of an aliphatic hydrocarbon, an alicyclic hydrocarbon, an aromatic hydrocarbon, an ether, a chlorinated hydrocarbon and a fluorine-containing solvent.

13. A process as claimed in claim 1, wherein the aqueous phase containing a thiocyanate ion is an aqueous solution in which an alkali metal or alkaline earth metal thiocyanate is dissolved.

14. A process as claimed in claim 13, wherein the alkali metal thiocyanate is sodium thiocyanate.

15. A process as claimed in claim 1, wherein the mole ratio of the thiocyanate ion in the aqueous phase to the quaternary onium fluorine-containing carboxylate in the organic phase is from 0.5 to 20.

16. A process as claimed in claim 1, wherein step (i) is conducted by a multistage counter-current contacting reaction system.

17. A process as claimed in claim 1, wherein the water-soluble oxidizing agent is an alkali metal hypochlorite or an alkaline earth metal hypochlorite.

18. A process as claimed in claim 17, wherein the alkali metal hypochlorite is sodium hypochlorite.

19. A process as claimed in claim 17, wherein the alkaline earth metal hypochlorite is calcium hypochlorite.

20. A process as claimed in claim 1, wherein the mole ratio of the water-soluble oxidizing agent in the aqueous solution to the quaternary onium thiocyanate in the organic phase is at least one.

* * * * *